United States Patent
Dietz et al.

(10) Patent No.: US 8,285,362 B2
(45) Date of Patent: Oct. 9, 2012

(54) CATHETER WITH DEFLECTABLE IMAGING DEVICE

(75) Inventors: Dennis R. Dietz, Littleton, CO (US); Paul N. Latulippe, Chino Valley, AZ (US); David J. Messick, Flagstaff, AZ (US); Craig T. Nordhausen, Parker, CO (US); Clyde G. Oakley, Centennial, CO (US); Ryan C. Patterson, Farmington, UT (US); Jim H. Polenske, Bellemont, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 1108 days.

(21) Appl. No.: 12/163,325

(22) Filed: Jun. 27, 2008

(65) Prior Publication Data
US 2009/0088631 A1    Apr. 2, 2009

Related U.S. Application Data

(60) Provisional application No. 60/946,807, filed on Jun. 28, 2007.

(51) Int. Cl.
*A61B 5/05* (2006.01)

(52) U.S. Cl. ........ 600/424; 600/437; 600/439; 600/462; 600/466

(58) Field of Classification Search .......... None
See application file for complete search history.

(56) References Cited

U.S. PATENT DOCUMENTS

| 3,955,561 A | 5/1976 | Eggleton |
| 4,059,098 A | 11/1977 | Murdock |
| 4,060,889 A | 12/1977 | Zielinski |
| 4,092,867 A | 6/1978 | Matzuk |
| 4,149,419 A | 4/1979 | Connell, Jr. et al. |
| 4,245,624 A | 1/1981 | Komiya |
| 4,316,271 A | 2/1982 | Evert |
| 4,327,738 A | 5/1982 | Green et al. |

(Continued)

FOREIGN PATENT DOCUMENTS

EP    0521595 A1    1/1993

(Continued)

OTHER PUBLICATIONS

Biocardia, Morph Vascular Access Catheter, (Publication Date Not Known), www.biocardia.com/morph/products.shtml, 2 pages.

(Continued)

*Primary Examiner* — Tse Chen
*Assistant Examiner* — Bradley Impink
(74) *Attorney, Agent, or Firm* — Richard W. Ellis

(57) ABSTRACT

An improved catheter is provided. The catheter may include a deflectable member located at a distal end of the catheter. The deflectable member may comprise an ultrasound transducer array. The catheter may include a lumen extending from a proximal end of the catheter to the distal end. The lumen may be used to deliver an interventional device to a point distal to the distal end of the catheter. The deflectable member may be selectively deflectable in a pivot-like manner through an arc of at least 90 degrees. In embodiments where the deflectable member includes an ultrasound transducer array, the ultrasound transducer array may be operable to image both when aligned with the catheter and when pivoted relative to the catheter. When pivoted relative to the catheter, the ultrasound transducer array may have a field of view distal to the distal end of the catheter.

20 Claims, 22 Drawing Sheets

U.S. PATENT DOCUMENTS

| | | | |
|---|---|---|---|
| 4,398,425 A | 8/1983 | Matzuk | |
| 4,399,703 A | 8/1983 | Matzuk | |
| 4,421,118 A | 12/1983 | Dow et al. | |
| 4,452,236 A | 6/1984 | Utsugi | |
| 4,455,872 A | 6/1984 | Kossoff et al. | |
| 4,474,184 A | 10/1984 | Harui | |
| 4,516,972 A | 5/1985 | Samson | |
| 4,559,951 A | 12/1985 | Dahl et al. | |
| 4,664,121 A | 5/1987 | Sanghvi et al. | |
| 4,747,411 A | 5/1988 | Ledley | |
| 4,756,313 A | 7/1988 | Terwilliger | |
| 4,784,148 A | 11/1988 | Dow et al. | |
| 4,794,930 A | 1/1989 | Machida et al. | |
| 4,841,979 A | 6/1989 | Dow et al. | |
| 4,895,158 A | 1/1990 | Kawabuchi et al. | |
| 4,977,898 A | 12/1990 | Schwarzschild et al. | |
| 4,995,868 A | 2/1991 | Brazier | |
| 5,030,204 A | 7/1991 | Badger et al. | |
| 5,070,879 A | 12/1991 | Herres | |
| 5,090,956 A | 2/1992 | McCoy | |
| 5,152,294 A | 10/1992 | Mochizuki et al. | |
| 5,159,931 A | 11/1992 | Pini | |
| 5,168,864 A | 12/1992 | Shockey | |
| 5,181,514 A | 1/1993 | Solomon et al. | |
| 5,191,890 A | 3/1993 | Hileman | |
| 5,226,422 A | 7/1993 | McKeighen et al. | |
| 5,255,668 A | 10/1993 | Umeda | |
| 5,268,531 A | 12/1993 | Nguyen et al. | |
| 5,291,896 A | 3/1994 | Fonger et al. | |
| 5,306,245 A | 4/1994 | Heaven | |
| 5,318,008 A | 6/1994 | Bullard | |
| 5,345,940 A | 9/1994 | Seward et al. | |
| 5,351,692 A | 10/1994 | Dow et al. | |
| 5,377,685 A | 1/1995 | Kazi et al. | |
| 5,379,772 A | 1/1995 | Imran | |
| 5,397,321 A | 3/1995 | Houser et al. | |
| 5,398,689 A | 3/1995 | Connor et al. | |
| 5,402,789 A | 4/1995 | Dow et al. | |
| 5,413,107 A | 5/1995 | Oakley et al. | |
| 5,427,107 A | 6/1995 | Milo et al. | |
| 5,454,795 A | 10/1995 | Samson | |
| 5,456,258 A | 10/1995 | Kondo et al. | |
| 5,460,168 A | 10/1995 | Masubuchi et al. | |
| 5,460,179 A | 10/1995 | Okunuki et al. | |
| 5,469,853 A | 11/1995 | Law et al. | |
| 5,485,845 A | 1/1996 | Verdonk et al. | |
| 5,486,162 A | 1/1996 | Brumbach | |
| 5,531,119 A | 7/1996 | Meyers | |
| 5,545,200 A | 8/1996 | West et al. | |
| 5,591,142 A | 1/1997 | Van Erp | |
| 5,630,806 A | 5/1997 | Inagaki et al. | |
| 5,651,364 A | 7/1997 | Yock | |
| 5,662,116 A | 9/1997 | Kondo et al. | |
| 5,662,621 A | 9/1997 | LaFontaine | |
| 5,681,280 A | 10/1997 | Rusk et al. | |
| 5,699,805 A | 12/1997 | Seward et al. | |
| 5,702,365 A | 12/1997 | King | |
| 5,779,643 A | 7/1998 | Lum et al. | |
| 5,842,473 A | 12/1998 | Fenster et al. | |
| 5,853,368 A | 12/1998 | Solomon et al. | |
| 5,876,386 A | 3/1999 | Samson | |
| 5,993,424 A | 11/1999 | Lorenzo et al. | |
| 6,004,269 A | 12/1999 | Crowley et al. | |
| 6,068,629 A | 5/2000 | Haissaguerre et al. | |
| 6,071,274 A * | 6/2000 | Thompson et al. | 604/528 |
| 6,090,104 A | 7/2000 | Webster, Jr. | |
| 6,099,464 A * | 8/2000 | Shimizu et al. | 600/104 |
| 6,126,606 A | 10/2000 | Bergstoel | |
| 6,149,599 A | 11/2000 | Schlesinger et al. | |
| 6,190,353 B1 | 2/2001 | Makower et al. | |
| 6,210,362 B1 | 4/2001 | Ponzi | |
| 6,213,948 B1 | 4/2001 | Barthe et al. | |
| 6,213,958 B1 | 4/2001 | Winder | |
| 6,231,514 B1 | 5/2001 | Lowe et al. | |
| 6,233,490 B1 | 5/2001 | Kasevich | |
| 6,254,568 B1 | 7/2001 | Ponzi | |
| 6,315,732 B1 | 11/2001 | Suorsa et al. | |
| 6,375,615 B1 | 4/2002 | Flaherty et al. | |
| 6,409,673 B2 | 6/2002 | Yock | |
| 6,443,944 B1 | 9/2002 | Doshi et al. | |
| 6,461,298 B1 | 10/2002 | Fenster et al. | |
| 6,572,547 B2 | 6/2003 | Miller et al. | |
| 6,585,718 B2 | 7/2003 | Hayzelden et al. | |
| 6,589,182 B1 | 7/2003 | Loftman et al. | |
| 6,592,520 B1 | 7/2003 | Peszynski et al. | |
| 6,592,526 B1 | 7/2003 | Lenker | |
| 6,645,152 B1 | 11/2003 | Jung et al. | |
| 6,679,849 B2 | 1/2004 | Miller et al. | |
| 6,689,066 B1 | 2/2004 | Omura et al. | |
| 6,709,396 B2 | 3/2004 | Flesch et al. | |
| 6,716,176 B1 | 4/2004 | Weston et al. | |
| 6,780,197 B2 | 8/2004 | Roe et al. | |
| 6,832,477 B2 | 12/2004 | Gummin et al. | |
| 6,908,434 B1 | 6/2005 | Jenkins et al. | |
| 6,939,338 B2 | 9/2005 | Waldhauser et al. | |
| 7,022,102 B2 | 4/2006 | Paskar | |
| 7,037,269 B2 | 5/2006 | Nix et al. | |
| 7,226,417 B1 | 6/2007 | Eberle et al. | |
| 7,232,433 B1 | 6/2007 | Schlesinger et al. | |
| 7,311,659 B2 | 12/2007 | Bob et al. | |
| 7,451,595 B2 | 11/2008 | Komori et al. | |
| 7,473,224 B2 | 1/2009 | Makin | |
| 7,494,469 B2 | 2/2009 | Bruestle | |
| 7,507,205 B2 | 3/2009 | Borovsky et al. | |
| 7,524,289 B2 | 4/2009 | Lenker | |
| 2001/0047165 A1 | 11/2001 | Makower et al. | |
| 2002/0049383 A1 | 4/2002 | Swanson et al. | |
| 2002/0062083 A1 | 5/2002 | Ohara et al. | |
| 2004/0006277 A1 | 1/2004 | Langenhove et al. | |
| 2004/0045735 A1 | 3/2004 | Varkey et al. | |
| 2004/0158153 A1 | 8/2004 | Hirt et al. | |
| 2004/0204650 A1 | 10/2004 | Taylor | |
| 2005/0015011 A1 | 1/2005 | Liard et al. | |
| 2005/0016753 A1 | 1/2005 | Seigerschmidt | |
| 2005/0027198 A1 | 2/2005 | Couvillon, Jr. | |
| 2005/0059957 A1 | 3/2005 | Campbell et al. | |
| 2005/0228290 A1 | 10/2005 | Borovsky et al. | |
| 2006/0085054 A1 | 4/2006 | Zikorus et al. | |
| 2006/0131061 A1 | 6/2006 | Seigerschmidt | |
| 2006/0184035 A1 | 8/2006 | Kimura et al. | |
| 2006/0224142 A1 | 10/2006 | Wilson et al. | |
| 2006/0235304 A1 | 10/2006 | Harhen et al. | |
| 2007/0016063 A1 | 1/2007 | Park et al. | |
| 2007/0073135 A1 | 3/2007 | Lee et al. | |
| 2007/0073151 A1 | 3/2007 | Lee | |
| 2007/0088323 A1 | 4/2007 | Campbell et al. | |
| 2007/0106144 A1 | 5/2007 | Squeri | |
| 2007/0106203 A1 | 5/2007 | Wilson et al. | |
| 2007/0118035 A1 | 5/2007 | Secora | |
| 2007/0167813 A1 | 7/2007 | Lee et al. | |
| 2007/0167821 A1 | 7/2007 | Lee et al. | |
| 2007/0167826 A1 | 7/2007 | Lee et al. | |
| 2007/0179380 A1 | 8/2007 | Grossman | |
| 2007/0204613 A1 | 9/2007 | Alacqua et al. | |
| 2007/0239010 A1 | 10/2007 | Johnson | |
| 2007/0239023 A1 | 10/2007 | Hastings et al. | |
| 2008/0004528 A1 | 1/2008 | Fitzsimons et al. | |
| 2008/0021408 A1 | 1/2008 | Jacobsen et al. | |
| 2008/0033292 A1 | 2/2008 | Shafran | |
| 2008/0097391 A1 | 4/2008 | Feinberg et al. | |
| 2008/0097403 A1 | 4/2008 | Donaldson et al. | |
| 2008/0287797 A1 | 11/2008 | Lee et al. | |
| 2008/0287862 A1 | 11/2008 | Weitzner et al. | |
| 2009/0000383 A1 | 1/2009 | Knowles et al. | |
| 2009/0093726 A1 | 4/2009 | Takayama et al. | |
| 2009/0118620 A1 | 5/2009 | Tgavalekos et al. | |
| 2009/0124857 A1 | 5/2009 | Viola | |
| 2009/0125019 A1 | 5/2009 | Douglass et al. | |
| 2009/0198219 A1 | 8/2009 | Campbell et al. | |
| 2009/0264759 A1 | 10/2009 | Byrd | |
| 2009/0264767 A1 | 10/2009 | Griffin et al. | |

FOREIGN PATENT DOCUMENTS

| | | |
|---|---|---|
| EP | 0 774 232 A1 | 5/1997 |
| EP | 829242 | 3/1998 |
| EP | 0982711 A2 | 3/2000 |
| JP | 1280446 A | 11/1989 |

| | | |
|---|---|---|
| JP | 1284233 A | 11/1989 |
| JP | 1284234 A | 11/1989 |
| JP | 2021852 A | 1/1991 |
| JP | 10216146 | 8/1998 |
| JP | 2003-190289 | 8/2003 |
| JP | 2004-135693 | 5/2004 |
| JP | 2005-195998 A | 7/2005 |
| WO | 91/13648 | 9/1991 |
| WO | 9113648 | 9/1991 |
| WO | 2005/099584 A2 | 10/2005 |

OTHER PUBLICATIONS

Bom, N.; Hoff, H. Ten; Lancee, C.T.; Gussenhoven, W.J. and Bosh, J.G.; Early and Recent Intraluminal Ultrasound Devices; International Journal of Cardiac Imaging 4: 79088, 10 Pages.

Lee, Warren; Idriss, Salim F.; Wolf, Patrick D. and Smith, Stephen W.; A Miniaturized Catheter 2-D Array for Real-Time, 3-D Intracardiac Echocardiography, IEEE Transactions on Ultrasonics, Ferroelectrics, and Frequency Control, vol. 51 No. 10, Oct. 2004, 13 Pages.

Lee, Warren; Idriss, Salim F.; Wolf, Patrick D. and Smith, Stephen W.; Dual Lumen Transducer Probes for Real-Time 3-D Interventional Cardiac Ultrasound, Ultrasound in Med. & Biol. vol. 29 No. 9, 2003, 8 Pages.

Light, Edward D.; Wolf, Patrick D. and Smith, Stephen W.; Two Dimensional Arrays for Real Time 3D Intracranial Imaging of the Brain; Department of Biomedical Engineering Duke Univrsity, 4 Pages.

Martin, Roy W. and Johnson, Christopher C.; Design Characteristics for Intravascular Ultrasonic Catheters; International Journal of Cardiac Imaging 4: 201-216, 1989, 15 Pages.

Seward, M.D, James B.; Packer, M.D., Douglas L.; Chan, M.D., Rodrigo C., Curley, Ph.D., Michael and Tajik, M.D., A. Jamil; Ultrasound Cardioscopy: Embarking on a New Journey, Mayo Clinic Proceedings vol. 71 No. 7, Jul. 1996, 7 Pages.

Siemens, Cardiology Solutions, Acuson AcuNav Diagnostic Ultrasound Catheter, (Publication Date Not Known) http://cardiology.usa.siemens.com/products-and-it-systems/cardiology-products/ultrasound/..., 2 Pages.

Strole, Jeff; Corbett, Scott; Lee, Warren; Light, Edward and Smith Stephen; A Novel Flex Circuit Area-Array Interconnect System for a Catheter-Based Ultrasound Transducer, MicroConnex, Inc., Sep. 5, 2002, 6 Pages.

www.eecs.umich.edu/~odonnell/images/acunav.jpg, (Publication Date Not Known), 1 Page.

Baker et al., Usefulness of Live Three-Dimensional Transesophageal Echocardiography in a Congenital Heart Disease Center, The American Journal of Cardiology, Apr. 1, 2009, pp. 1025-1028, vol. 103, Issue 7, Elsevier Inc., USA.

Green et al., Initial Clinical Experience With Intracardiac Echocardiography in Guiding Balloon Mitral Valvuloplasty: Technique, Safety, Utility, and Limitations, Catherterization and Cardiovascular Interventions, 2004, pp. 385-394, vol. 63, No. 3, Wiley-Liss, USA.

Huang, Weimin, Shape Memory Alloys and their Application to Actuators for Deployable Structures, University of Cambridge Department of Engineering, Mar. 1998, 192 pages, Peterhouse, USA.

Knackstedt et al., Semi-automated 3-dimensional intracardiac echocardiography: Development and initial clinical experience of a new system to guide ablation procedures. Heart Rhythm, Dec. 2006, pp. 1453-1459, vol. 3, No. 12, Elsevier Inc.

Kottenstette, Nicholas E., Designing Mechanisms with Shape Memory Alloys and Permanent Magnets, 162 pages, Massachusetts Institute of Technology, 162, pages, Feb. 1997, USA.

Matzuk, T. and Skolnick, M.L., Novel ultrasonic real-time scanner featuring servo controlled transducers displaying a sector image, Ultrasonics, Jul. 1978, pp. 171-178.

Song, G., Design and control of a Nitinol wire actuated rotary servo, Smart Materials and Structures, Sep. 5, 2007, pp. 1796-1801, vol. 16, IPO Publishing, UK.

Zara et al., Intracardiac Ultrasound Scanner Using a Micromachine (MEMS) Actuator, IEEE Transactions on Ultrasonics, Ferroelectrics, and Frequency Control, Jul. 2000, pp. 984-993, vol. 47, No. 4, IEEE Ultrasonics, Ferroelectrics, and Frequency Control Society.

\* cited by examiner

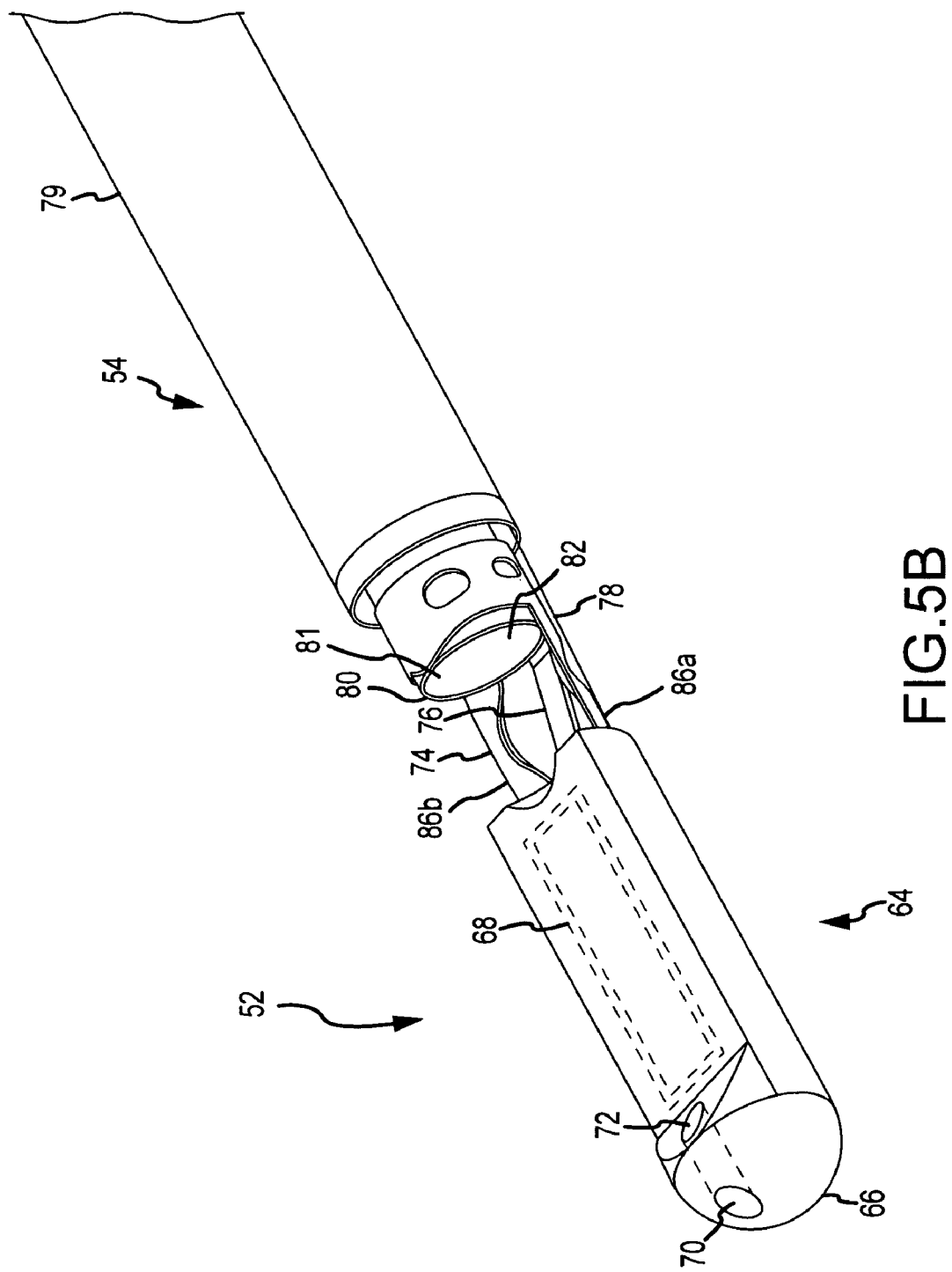

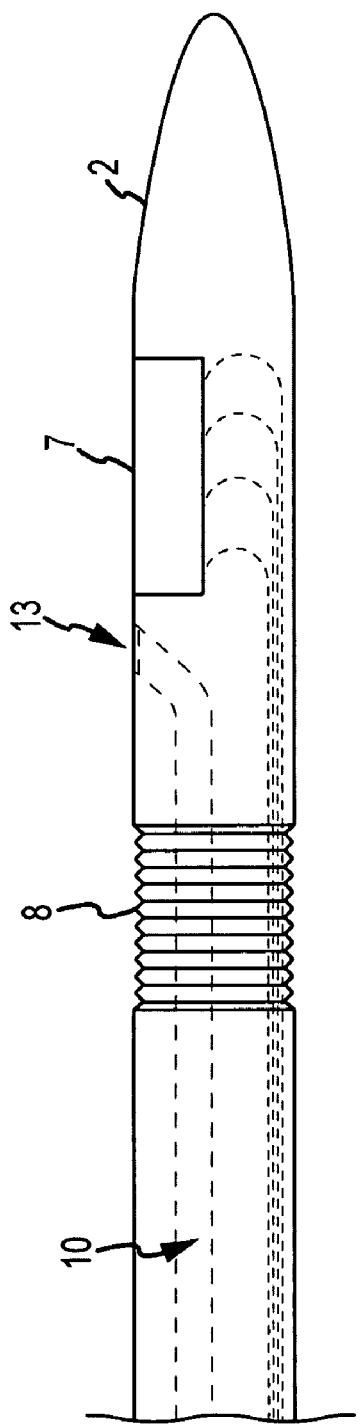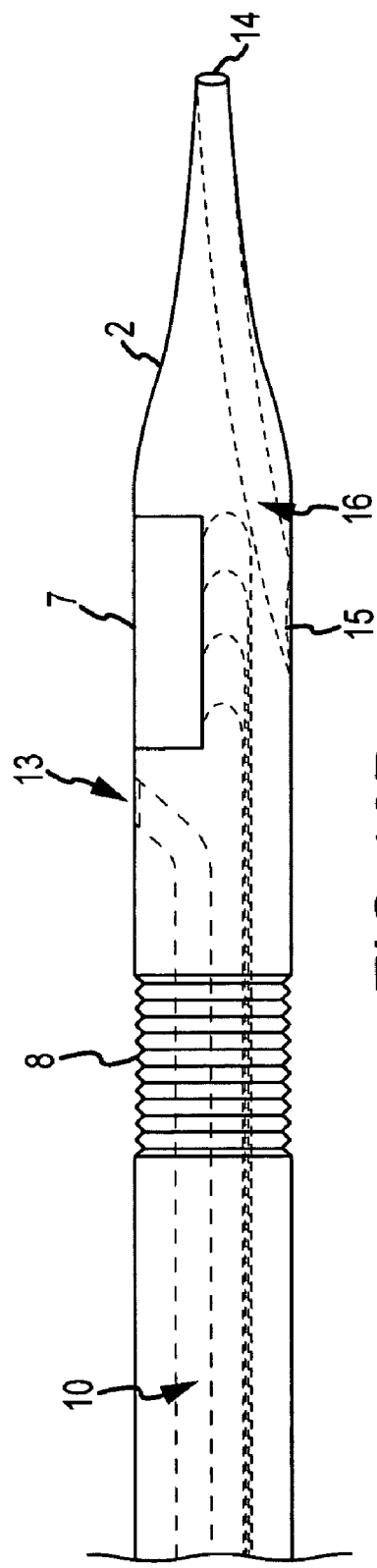

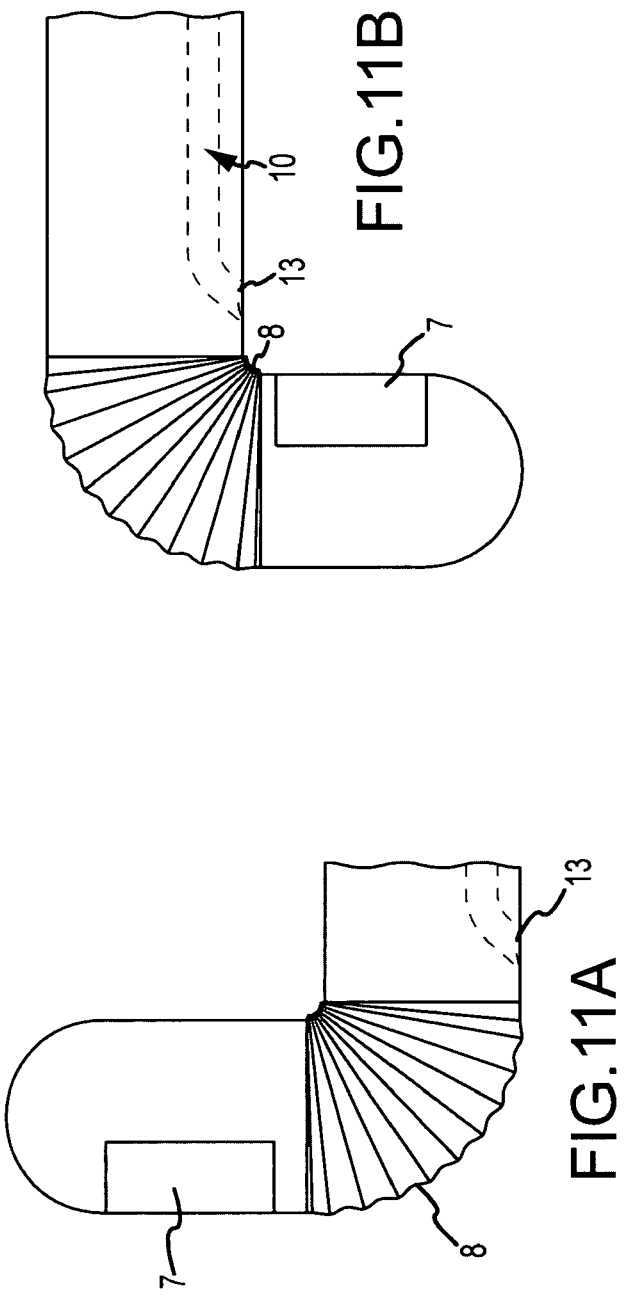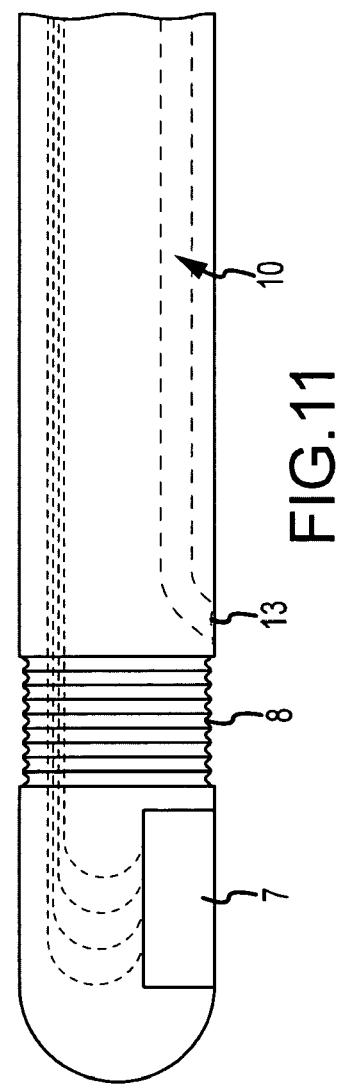

CATHETER WITH DEFLECTABLE IMAGING DEVICE

RELATED APPLICATIONS

This application claims priority to U.S. Provisional Application Ser. No. 60/946,807, filed Jun. 28, 2007, entitled "ULTRASOUND CATHETER", the entirety of which is hereby incorporated by reference.

FIELD OF THE INVENTION

The invention relates to improved catheters, and is particularly apt to catheters for imaging and interventional device delivery (e.g. ultrasound catheters with diagnostic or therapeutic device, agent or energy delivery capabilities) that can be used to obtain targeted images of interventional devices positioned at desired locations in the body of a patient and/or delivery target locations.

BACKGROUND OF THE INVENTION

Catheters are tubular medical devices that may be inserted into a body vessel, cavity or duct, and manipulated utilizing a portion that extends out of the body. Typically, catheters are relatively thin and flexible to facilitate advancement/retraction along non-linear paths. Catheters may be employed for a wide variety of purposes, including the internal bodily positioning of diagnostic and/or therapeutic devices. For example, catheters may be employed to position internal imaging devices, deploy implantable devices (e.g., stents, stent grafts, vena cava filters), and/or deliver energy (e.g., ablation catheters).

In this regard, use of ultrasonic imaging techniques to obtain visible images of structures is increasingly common, particularly in medical applications. Broadly stated, an ultrasonic transducer, typically comprising a number of individually actuated piezoelectric elements, is provided with suitable drive signals such that a pulse of ultrasonic energy travels into the body of the patient. The ultrasonic energy is reflected at interfaces between structures of varying acoustic impedance. The same or a different transducer detects the receipt of the return energy and provides a corresponding output signal. This signal can be processed in a known manner to yield an image, visible on a display screen, of the interfaces between the structures and hence of the structures themselves.

Numerous prior art patents discuss the use of ultrasonic imaging in combination with specialized surgical equipment in order to perform very precise surgical procedures. For example, a number of patents show use of ultrasonic techniques for guiding a "biopsy gun", i.e., an instrument for taking a tissue sample from a particular area for pathological examination, for example, to determine whether a particular structure is a malignant tumor or the like. Similarly, other prior art patents discuss use of ultrasonic imaging techniques to assist in other delicate operations, e.g., removal of viable eggs for in vitro fertilization, and for related purposes.

As internal diagnostic and therapeutic procedures continue to evolve, the desirability of enhanced procedure imaging via compact and maneuverable catheters has been recognized. More particularly, the present inventors have recognized the desirability of providing catheter features that facilitate selective positioning and control of componentry located at a distal end of a catheter, while maintaining a relatively small profile, thereby yielding enhanced functionality for various clinical applications.

SUMMARY OF THE INVENTION

The present invention relates to improved catheter designs. For purposes hereof, a catheter is defined as a device which is capable of being inserted into a body vessel, cavity or duct, wherein at least a portion of the catheter extends out of the body and the catheter is capable of being manipulated and/or removed from the body by manipulating/pulling on the portion of the catheter extending out of the body. In the various designs the catheter comprises an outer tubular body having a wall, a proximal end and a distal end. The catheter may further include a deflectable member located at the distal end of the outer tubular body. The deflectable member may include one or more therapeutic and/or diagnostic devices. For example, the deflectable member may include an imaging device such as an ultrasound transducer array. Further, the ultrasound transducer array may be a one dimensional array, one and a half dimensional array, or a two dimensional array. The deflectable member may be selectively deflectable relative to the outer tubular body to facilitate operation of componentry comprising the deflectable member.

In an additional aspect, at least a portion of the deflectable member may be permanently located outside of the outer tubular body. In this regard, the deflectable member may be selectively deflectable away from a center axis of the outer tubular body. In certain embodiments, such deflectability may be at least partially or entirely distal to the distal end of the outer tubular body.

In one aspect, the catheter may also include a lumen for delivering an interventional device extending through the outer tubular body from the proximal end of the outer tubular body to a point distal thereto. For purposes hereof, "interventional device" includes without limitation diagnostic devices (e.g. pressure transducers, conductivity measurement devices, temperature measurement devices, flow measurement devices, electro- and neuro-physiology mapping devices, material detection devices, imaging devices, central venous pressure (CVP) monitoring devices, intracardiac echocardiography (ICE) catheters, balloon sizing catheters, needles, biopsy tools), therapeutic devices (e.g. ablation catheters (e.g., radio-frequency, ultrasonic, optical), patent foramen ovale (PFO) closure devices, cryotherapy catheters, vena cava filters, stents, stent-grafts, septostomy tools), and agent delivery devices (e.g., needles, cannulae, catheters, elongated members). For purposes hereof, "agent" includes without limitation therapeutic agents, pharmaceuticals, chemical compounds, biologic compounds, genetic materials, dyes, saline, and contrast agents. The agent may be liquid, gel, solid, or any other appropriate form. Furthermore, the lumen may be used to delivery agents therethrough without the use of an interventional device. The combinative inclusion of a deflectable member and lumen for interventional device delivery therethrough facilitates multi-functionality of the catheter. This is advantageous because it reduces the number of catheters and access sites required during the procedure, provides the potential to limit the interventional procedure time, and enhances ease of use.

In this regard, in certain embodiments the lumen may be defined by an inside surface of the wall of the outer tubular body. In other embodiments, the lumen may be defined by an inside surface of an inner tubular body located within the outer tubular body and extending from the proximal end to the distal end thereof.

In another aspect, a deflectable member may be selectively deflectable through an arc of at least 45 degrees, and in various implementations at least 90 degrees. For example, the deflectable member may be deflectable in a pivot-like manner about a pivot, or hinge, axis through an arc of at least 90 degrees. Further, the deflectable member may be selectively deflectable and maintainable at a plurality of positions across a range of different angled positions. Such embodiments are particularly apt for implementing a deflectable member comprising an imaging device.

In certain embodiments, a deflectable imaging device may be selectively deflectable from an exposed (e.g., where at least a portion of the aperture of the deflectable imaging device is free from interference from the outer tubular body) side-looking first position to an exposed forward-looking, second position. "Side-looking" as used herein is defined as the position of the deflectable imaging device where the field of view of the deflectable imaging device is oriented substantially perpendicular to the distal end of the outer tubular body. "Forward-looking" includes where the imaging field of view of the deflectable imaging device is at least partially deflected to enable imaging of a volume distal to the distal end of the catheter. For example, a deflectable imaging device (e.g., an ultrasound transducer array) may be aligned with (e.g., disposed parallel to or coaxially with) a center axis of the outer tubular body in a first position. Such an approach accommodates imaging of anatomical landmarks during catheter positioning (e.g. during insertion and advancement of the catheter into a vascular passageway or bodily cavity), wherein anatomical landmark images may be employed to precisely position an exit port of a lumen comprising the catheter. In turn, the ultrasound transducer array may be deflected from the side-looking, first position to a forward-looking, second position (e.g., angled at least 45 degrees, or in some applications at least 90 degrees) relative to a center axis of the catheter. An interventional device may then be selectively advanced through a lumen of the catheter and into a work area located adjacent to a lumen exit port and within an imaging field of view of the ultrasound transducer array, wherein imaged internal procedures may be completed utilizing the interventional device with imaging from the ultrasound transducer array alone or in combination with other imaging modalities (e.g., fluoroscopy). The deflectable imaging device may be deflected such that no part of the deflectable imaging device occupies a volume with the same cross section as the exit port and extending distally from the exit port. As such, the imaging field of view of the deflectable imaging device may be maintained in a fixed registration relative to the outer tubular body while the interventional device is being advanced through the outer tubular body, through the exit port, and into the imaging field of view of the deflectable imaging device.

In a related aspect, a deflectable member may comprise an ultrasound transducer array having an aperture length at least as large as a maximum cross-dimension of the outer tubular body. Correspondingly, the deflectable ultrasound transducer array may be provided for selective deflection from a first position that accommodates advancement of the catheter through a vascular passageway to a second position that is angled relative to the first position. Again, in certain embodiments the second position may be selectively established by a user.

In a related aspect, deflectable member may be deflectable from a first position aligned with the center axis of the catheter (e.g. parallel thereto) to a second position angled relative to the center axis, wherein when in the second position the deflectable member is disposed outside of a working area located adjacent to a lumen exit port. As such, an interventional device may be advanceable through the exit port free from interference with the deflectable member.

In certain embodiments, the deflectable member may be provided so that the cross-sectional configuration thereof generally coincides with the cross-sectional configuration of the outer tubular body at the distal end thereof. For example, when a cylindrically-shaped outer tubular body is employed, a deflectable member may be located beyond the distal end of the outer tubular body and configured to coincide with (e.g., slightly exceed, occupy, or fit within) an imaginary cylindrical volume defined by and adjacent to such distal end, wherein the deflectable member is selectively deflectable out of such volume. Such an approach facilitates initial advancement and positioning of the catheter through vascular passageways.

In certain embodiments, a deflectable member may be provided to deflect along an arc path that extends away from a center axis of the outer tubular body. By way of example, in various implementations the deflectable member may be disposed to deflect from a first position that is located distal to a lumen exit port, to a second position that is lateral to the outer tubular body (e.g. to one side of the outer tubular body).

In another aspect, a deflectable member may be provided to deflect from a longitudinal axis of the catheter, wherein upon deflection a displacement arc is defined. In a catheter with a tip fixed relative to the outer tubular body, the displacement arc is the minimum curvature of the catheter. In a catheter with a deflectable member movable relative to the outer tubular body, the displacement arc is the minimum arc that is tangent to a face of the deflectable member and tangent to the center axis of the catheter. In the present aspect, a deflectable member may be provided wherein a ratio of a maximum cross-dimension of the distal end of the outer tubular body to the displacement arc radius is at least about 1. By way of example, for a cylindrical outer tubular body, the ratio may be defined by the outer diameter of the distal end of the outer tubular body over the displacement arc radius, wherein such ratio may be advantageously established to be at least about 1.

In another aspect, a deflectable member may be interconnected to the catheter body wall at the distal end of the outer tubular body. As will be further described, such interconnection may provide support functionality and/or selective deflection functionality. In the latter regard, the deflectable member may be deflectable about a deflection axis that is offset from a center axis of the outer tubular body. For example, the deflection axis may lie in a plane that extends transverse to the center axis of an outer tubular body and/or in a plane that extends parallel to the center axis. In the former regard, in one embodiment the deflection axis may lie in a plane that extends orthogonal to the center axis. In certain implementations, the deflection axis may lie in a plane that extends tangent to an exit port of a lumen that extends through the outer tubular body of the catheter.

In yet another aspect, the catheter may comprise a lumen for delivering an interventional device extending from the proximal end to an exit port located at the distal end of the outer tubular body, wherein the exit port has a center axis coaxially aligned with a center axis of the outer tubular body. Such an arrangement facilitates the realization of relatively small catheter cross-dimensions, thereby enhancing catheter positioning (e.g. within small and/or tortuous vascular passageways). The deflectable member may also be disposed for deflection away from the coaxial center axes, thereby facilitating angled lateral positioning away from the initial catheter introduction (e.g., 0 degree) position of the deflectable member. In certain embodiments, the deflectable member may be deflectable through an arc of at least 90 degrees.

In a further aspect, the catheter may include an actuation device, extending from the proximal end to the distal end of the outer tubular body, wherein the actuation device may be interconnected to the deflectable member. Actuation devices may include devices selected from the group consisting of balloons, tether lines, pull wires, hypotubes, or stylets. The actuation device and outer tubular body may be disposed for relative movement such that the deflectable member is deflectable through an arc of at least 45 degrees in response to 0.5 cm or less relative movement between the actuation device and the outer tubular body. By way of example, in certain embodiments the deflectable member may be deflectable through an arc of at least 90 degrees in response to 1.0 cm or less relative movement of the actuation device and outer tubular body.

In a further aspect, the deflectable member may be interconnected to the outer tubular body. In one approach, the deflectable member may be supportably interconnected to the outer tubular body at the distal end thereof. In turn, an actuation device comprising one or more elongate members (e.g. of wire-like construction) may be disposed along the outer tubular body and interconnected at a distal end to the deflectable member, wherein upon applying a tensile force (e.g. a pull force) to a proximal end of the elongate member(s) the distal end of the elongate member(s) may cause the deflectable member to deflect. In this approach, the outer tubular body may define a lumen therethrough for delivering an interventional device extending from the proximal end of the outer tubular body to an exit port located distal to the proximal end.

In another approach, a deflectable member may be supportably interconnected to one of the outer tubular body and an actuation device, and restrainably interconnected by a restraining member (e.g. a ligature) to the other one of the outer tubular body and actuation device, wherein upon relative movement of the outer tubular body and actuation device the restraining member restrains movement of the deflectable member to affect deflection thereof.

For example, the deflectable member may be supportably interconnected to an actuation device and restrainably interconnected to the outer tubular body at the distal end thereof. In this approach, the actuation device may comprise an inner tubular body defining a lumen therethrough for delivering an interventional device extending from the proximal end of the catheter body to an exit port located distal to the proximal end.

More particularly, and in a further aspect, the catheter may comprise an inner tubular body, disposed within the outer tubular body for relative movement therebetween (e.g., relative slidable movement). A deflectable member located at the distal end may be supportably interconnected to the inner tubular body. In certain embodiments, the deflectable member may be disposed so that upon selective relative movement of the outer tubular body and inner tubular body the deflectable member is selectively deflectable and maintainable in a desired angular orientation.

For example, in one implementation an inner tubular body may be slidably advanced and retracted relative to an outer tubular body, wherein engagement between surfaces of the two components provides a mechanism interface sufficient to maintain a selected relative position of the two components and corresponding deflected position of the deflectable member. A proximal handle may also be provided to facilitate the maintenance of selected relative positioning of the two components.

In an additional aspect, the catheter may include an actuation device, extending from a proximal end to a distal end of the outer tubular body and moveable relative to the outer tubular body to apply a deflection force to the deflectable member. In this regard, the actuation device may be provided so that deflection force is communicated by the actuation device from the proximal end to the distal end in a balanced and distributed manner about a center axis of the outer tubular body. As may be appreciated, such balanced and distributed force communication facilitates the realization of a non-biased catheter yielding enhanced control and positioning attributes.

In conjunction with one or more of the above-noted aspects, the catheter may include a hinge that is supportably interconnected to the outer tubular body or, in certain embodiments, to an included actuation device (e.g. an inner tubular body). The hinge may be structurally separate from and fixedly interconnected to the catheter body (e.g., the outer tubular body or the inner tubular body). The hinge may be further fixedly interconnected to the deflectable member, wherein the deflectable member is deflectable in a pivot-like manner. The hinge member may be at least partially elastically deformable to deform from a first configuration to a second configuration upon the application of a predetermined actuation force, and to at least partially return from the second configuration to the first configuration upon removal of the predetermined actuation force. Such functionality facilitates the provision of a deflectable member that may be selectively actuated via an actuation device to move from an initial first position to a desired second position upon the application of a predetermined actuation force (e.g. a tensile or pulling force, or a compressive pushing force applied thereto), wherein upon selective release of the actuation force the deflectable member may automatically at least partially retract to its initial first position. In turn, successive deflectable positioning/retraction of the deflectable member may be realized during a given procedure, thereby yielding enhanced functionality in various clinical applications.

In certain embodiments, the hinge member may be provided to have a column strength sufficient to reduce unintended deflection of the deflectable member during positioning of the catheter (e.g. due to mechanical resistance associated with advancement of the catheter). By way of example, the hinge member may exhibit a column strength at least equivalent to that of the outer tubular body.

In certain implementations the hinge may be a portion of a one-piece, integrally defined member. For example, the hinge may comprise a shape memory material (e.g., Nitinol). In one approach, the hinge member may include a curved first portion and a second portion interconnected thereto, wherein the second portion is deflectable about a deflection axis defined by the curved first portion. By way of example, the curved first portion may comprise a cylindrically-shaped surface. In one embodiment, the curved first portion may include two cylindrically-shaped surfaces having corresponding center axes that extend in a common plane and intersect at an angle, wherein a shallow, saddle-like configuration is defined by the two cylindrically-shaped surfaces.

In yet a further aspect, the outer tubular body may be constructed to facilitate the inclusion of electrical componentry at the distal end thereof. More particularly, the outer tubular body may comprise a plurality of interconnected electrical conductors extending from the proximal end to the distal end. For example, in certain embodiments the electrical conductors may be interconnected in a ribbon-shaped member that is helically disposed about and along all or at least a portion of a catheter center axis, thereby yielding enhanced structurally qualities to the wall of the outer tubular body and avoiding excessive strain on the electrical conductors during flexure of the outer tubular body. For example, in certain embodiments the electrical conductors may be braided along at least a portion of the catheter center axis, thereby yielding enhanced structurally qualities to the wall of the outer tubular body. The outer tubular body may further include a first layer disposed inside of the first plurality of electrical conductors and extending from the proximal end to the distal end, and a second layer disposed on the outside of the first plurality of electrical conductors, extending from the proximal end to the distal end. The first tubular layer and second tubular layer may each be provided to have a dielectric constant of about 2.1 or less, wherein capacitive coupling may be advantageously reduced between the plurality of electrical conductors and bodily fluids present outside of the catheter and within a lumen extending through the outer tubular body.

In another aspect, the outer tubular body may comprise a plurality of electrical conductors extending from a proximal end to the distal end and a set of tubular layers inside and/or outside of the first plurality of electrical conductors. The set of tubular layers may comprise a low dielectric constant layer (e.g., located closest to the electrical conductors), and a high withstand voltage layer. In this regard, the low dielectric constant layer may have a dielectric constant of 2.1 or less, and the high withstand voltage layer may be provided to yield a withstand voltage of at least about 2500 volts AC. In certain embodiments, a set of low dielectric and high withstand voltage layers may be provided both inside and outside of the plurality of electrical conductors along the length of the outer tubular body.

In certain embodiments tie layers may be interposed between the electrical conductors and one or more inner and/or outer layers. By way of example, such tie layers may comprise a film material that may have a melt temperature that is lower than other components of the outer tubular body, wherein the noted layers of components may be assembled and the tie layers selectively melted to yield an interconnected structure. Such selectively melted tie layers may prevent other layers of the outer tubular body from migrating relative to each other during manipulation of the outer tubular body (e.g., during insertion into a patient).

For some arrangements, the outer tubular body may further include a shielding layer disposed outside of the electrical conductors. By way example, the shielding layer may be provided to reduce electromagnetic interference (EMI) emissions from the catheter as well as shield the catheter from external EMI.

In certain embodiments, lubricious inside and outside layers and/or coatings may also be included. That is, an inner layer may be disposed within the first tubular layer and an outer layer may be disposed outside of the second tubular layer.

In yet a further aspect, the catheter may be provided to comprise a first electrical conductor portion extending from a proximal end to a distal end of the catheter, and a second electrical conductor portion electrically interconnected to the first electrical conductive portion at the distal end. The first electrical conductor portion may comprise a plurality of interconnected electrical conductors arranged side-by-side with electrically non-conductive material therebetween. In certain implementations, the first electrical conductor portion may be helically disposed about a catheter center axis from the proximal end to the distal end thereof. In conjunction with such implementations, the second electrical conductor portion may comprise a plurality of electrical conductors interconnected to the plurality of interconnected electrical conductors of the first electrical conductor portion, and extending parallel to a center axis of the outer tubular body at the distal end. In certain embodiments, the first electrical conductor portion may be defined by a ribbon-shaped member included within the wall of the outer tubular body, thereby contributing to the structural integrity thereof.

In conjunction with the noted aspect, the first electrical conductor portion may define a first width across the interconnected plurality of electrical conductors, and the second electrical conductor portion may define a second width across the corresponding plurality of electrical conductors. In this regard, the second electrical conductor portion may be defined by electrically conductive traces disposed on a substrate. By way of example, the substrate may extend between the end of the first electrical conductor portion and electrical componentry provided at the distal end of a catheter, including for example an ultrasound transducer array.

In various embodiments, the second electrical conductor portion may be interconnected to a deflectable member and may be of a bendable construction, wherein at least a portion of the second electrical conductor portion is bendable with and in response to deflection of the deflectable member. More particularly, the second electrical conductor portion may be defined by electrically conductive traces on a substrate that is bendable in tandem with a deflectable member through an arc of at least 90 degrees.

In a further aspect, the catheter may comprise a deflectable member that includes an ultrasound transducer array, wherein at least a portion of the deflectable ultrasound transducer array may be located within the outer tubular body wall at the distal end. Further, the catheter may include a lumen for delivering an interventional device extending from the proximal end to a point distal thereto.

In a still further aspect, the catheter may comprise a steerable or pre-curved catheter segment located near the distal end of the outer tubular body and the deflectable member may comprise an ultrasound transducer array. Further, the catheter may include a lumen for delivering an interventional device extending from the proximal end to a point distal thereto.

In another aspect, the catheter may comprise an outer tubular body having a wall, a proximal end and a distal end. The catheter may further include a lumen for delivering an interventional device extending through the outer tubular body from the proximal end to an exit port located distal to the proximal end. The catheter may further include a first electrical conductor portion comprising a plurality of interconnected electrical conductors arranged side-by-side with electrically non-conductive material therebetween. The first electrical conductor portion may extend from the proximal end to the distal end. The catheter may further include a second electrical conductor portion electrically interconnected to the first electrical conductor portion at the distal end. The second electrical conductor portion may comprise a plurality of electrical conductors. The catheter may further include a deflectable member located at the distal end. The second electrical conductor portion may be electrically interconnected to the deflectable member and may be bendable in response to deflection of the deflectable member.

In another aspect, the catheter may comprise an outer tubular body having a wall, a proximal end and a distal end. The catheter may further include a lumen for delivering an interventional device or agent delivery device extending through the outer tubular body from the proximal end to an exit port located distal to the proximal end. The catheter may further include a deflectable member, at least a portion of which is permanently located outside of the outer tubular body at the distal end, selectively deflectable relative to the outer tubular body and distal to the exit port. In an embodiment, the catheter may further include a hinge located at the distal end where the deflectable member may be supportably interconnected to the hinge. In such an embodiment, the deflectable member may be selectively deflectable relative to the outer tubular body about a hinge axis defined by the hinge.

Numerous aspects described hereinabove comprising a selectively deflectable imaging device disposed at a distal end of an outer tubular body of a catheter. Additional aspects of the present invention may include deflectable members in place of such deflectable imaging devices. Such deflectable members may include imaging devices, diagnostic devices, therapeutic devices, or any combination thereof.

In another aspect, a method is provided for operating a catheter having a deflectable imaging device located at a distal end thereof. The method may include moving the distal end of the catheter from an initial position to a desired position and obtaining image data from the deflectable imaging device during at least a portion of the moving step. The deflectable imaging device may be located in a first position during the moving step. The method may further include utilizing the image data to determine when the catheter is located at the desired position, deflecting the deflectable imaging device from the first position to a second position after the moving step; and advancing an interventional device through an exit port at the distal end of the catheter and into an imaging field of view of the deflectable imaging device in the second position.

In an arrangement, the deflecting step may further include translating a proximal end of at least one of an outer tubular body of the catheter and actuation device of the catheter relative to a proximal end of the other one of the outer tubular body and actuation device.

A deflection force may be applied to a hinge in response to the translating step. The deflectable imaging device may be supportably interconnected by the hinge to one of the outer tubular body and the actuation device. The deflection force may be initiated in response to the translating step. The deflection force may be communicated in a balanced and distributed manner about a center axis of the outer tubular body.

In an arrangement, the position of the deflectable imaging device may be maintained relative to the distal end of the catheter during the moving and obtaining steps. In an embodiment, the deflectable imaging device may be side-looking in the first position and forward-looking in the second position. In an embodiment, the imaging field of view may be maintained in substantially fixed registration to the distal end of the catheter during the advancing step.

The various features discussed above in relation to each aforementioned aspect may be utilized by any of the aforementioned aspects. Additional aspects and corresponding advantages will be apparent to those skilled in the art upon consideration of the further description that follows.

BRIEF DESCRIPTION OF THE DRAWINGS

FIGS. 5B through 5E show an embodiment of a catheter that includes a deflectable member wherein the deflectable member is deflectable by moving an inner tubular body relative to an outer tubular body.

FIGS. 10A and 10B demonstrate further alternative embodiments.

FIGS. 11, 11A and 11B demonstrate further embodiments.

DETAILED DESCRIPTION OF THE DRAWINGS

Figure 1:
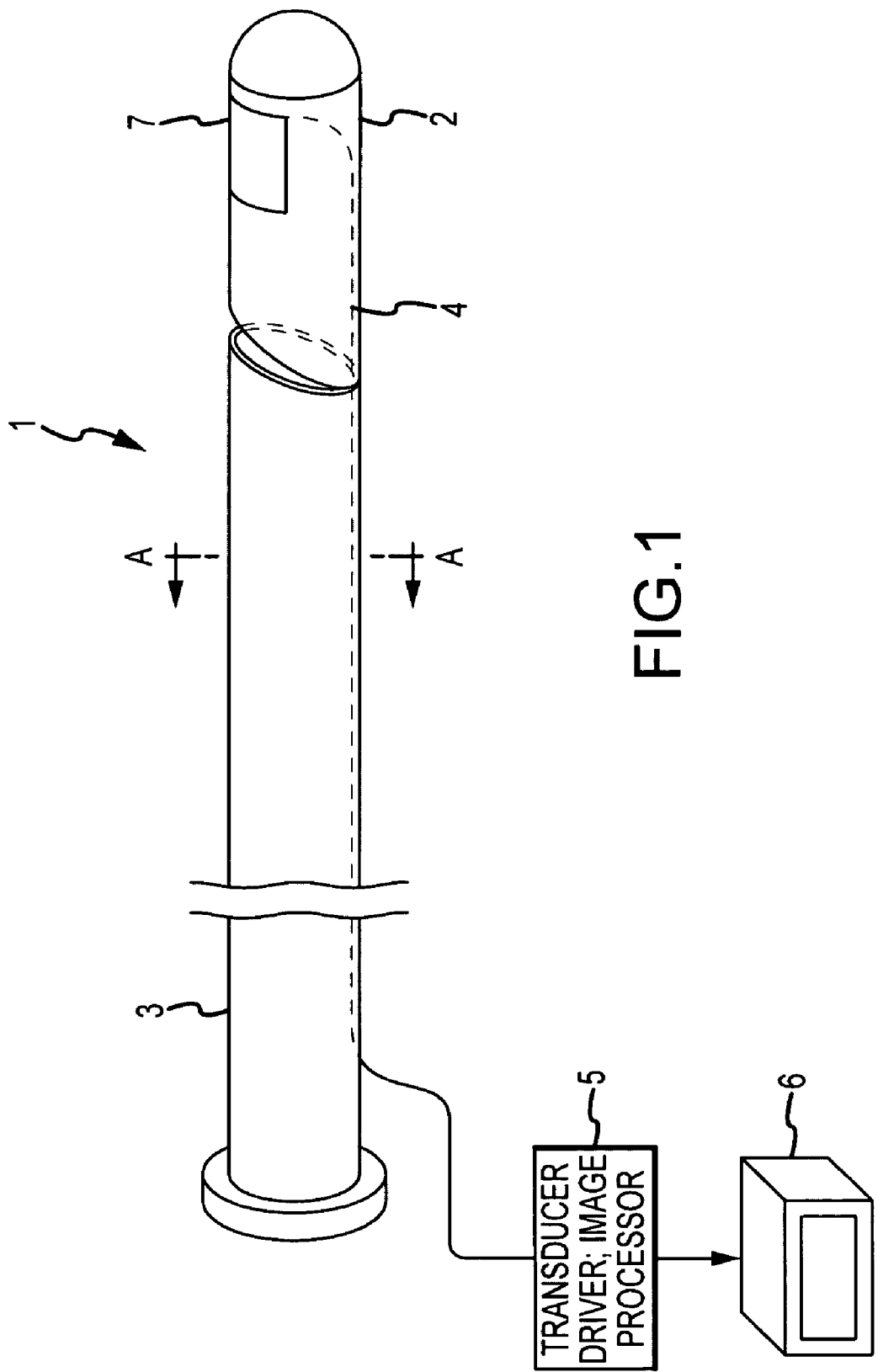
FIG. 1 shows a catheter embodiment having a deflectable ultrasound transducer array located at an end of the catheter.

The detailed description that follows is directed to various catheter embodiments that include a deflectable member that comprises an ultrasound transducer array, and a lumen for delivering an interventional device. Such embodiments are for exemplarily purposes and are not intended to limit the scope of the present invention. In that regard, the deflectable member may comprise componentry other than or in addition to an ultrasound transducer array. Further, additional embodiments may utilize inventive features described herein that do not necessitate the inclusion of a lumen.

An ultrasound transducer array built into a catheter presents unique design challenges. Two critical points include, for example, the resolution in the image plane and the ability to align that image plane with an interventional device.

The resolution in the imaging plane of an ultrasound array can be approximated by the following equation:

$$\text{Lateral resolution} = \text{Constant} * \text{wavelength} * \text{Image Depth} / \text{Aperture Length}$$

For catheters being described here, the wavelength is typically in the range of 0.2 mm (at 7.5 MHz). The constant is in the range of 2.0. The ratio of (Image Depth/Aperture Length) is a critical parameter. For ultrasound imaging in the range of 5-10 MHz for catheters presented here, acceptable resolution in the imaging plane can be achieved when this ratio is in the range of 10 or less.

For imaging with a catheter in the major vessels and the heart, it is desirable to image at depths of 70 to 100 mm. Catheters used in the heart and major vessels are typically 3 to 4 mm in diameter or smaller. Thus while conceptually a transducer array can be made of arbitrary size and placed at any position within the catheter body, this model shows that transducer arrays that readily fit within the catheter structure do not have sufficient width for acceptable imaging.

The ultrasound image plane produced by the array placed on the catheter typically has a narrow width typically called the out of plane image width. For objects to be seen in the ultrasound image, it is important that they be in this image plane. When a flexible/bendable catheter is placed in a major vessel or heart, the image plane can be aligned to some degree. It is desirable to guide a second device placed in the body with the ultrasound image, but doing so requires placing that second device in the plane of the ultrasound image. If the imaging array and the interventional device are both on flexible/bendable catheters that are inserted into the body, it is extremely difficult to orient one interventional device into the ultrasound image plane of the imaging catheter.

Certain embodiments of the present invention utilize an ultrasound image to guide an interventional device. To accomplish this, a large enough aperture is needed to produce an image of acceptable resolution while being able to place the device in a known position that is stable relative to the imaging array and/or to be able to align and/or register the interventional device to the ultrasound image plane.

In certain implementations, the aperture length of the ultrasound array may be larger than the maximum cross dimension of the catheter. In certain implementations, the aperture length of the ultrasound array may be much larger (2 to 3 times larger) than the diameter of the catheter. This large transducer, however, may fit within the 3 to 4 mm maximum diameter of the catheter to be inserted into the body. Once in the body, the imaging array is deployed out of the catheter body leaving space to pass an interventional device through that same catheter that will then be located in a known position relative to the imaging array. In certain arrangements, the imaging array may be deployed in a way so that the interventional device can be readily kept within the ultrasound image plane.

The catheter may be configured for delivery through a skin puncture at a remote vascular access site (e.g., vessel in the leg). Through this vascular access site, the catheter may be introduced into regions of the cardiovascular system such as the inferior vena cava, heart chambers, abdominal aorta, and thoracic aorta.

Positioning the catheter in these anatomic locations provides a conduit for delivery of devices or therapy to specific target tissues or structures. One example of this includes bedside delivery of inferior vena cava filters in patients for whom transport to the catheterization laboratory is either high risk or otherwise undesirable. The catheter with the ultrasound transducer array allows the clinician to not only identify the correct anatomical location for placement of the inferior vena cava filter, but also provides a lumen through which the vena cava filter can be delivered under direct ultrasound visualization. Both location identification and delivery of a device can occur without withdrawal or exchange of the catheter and/or imaging device. In addition, post-delivery visualization of the device allows the clinician to verify placement location and function(s) prior to removal of the catheter.

Another application of such a catheter is as a conduit through which ablation catheters can be delivered within the atria of the heart. Although ultrasound imaging catheters are utilized today in many of these cardiac ablation procedures, it is very difficult to achieve proper orientation of the ablation catheters and ultrasound catheter so as to attain adequate visualization of the ablation site. The catheter described herein provides a lumen through which the ablation catheter can be directed and the position of the ablation catheter tip monitored under direct ultrasound visualization. As described, the coaxial registration of this catheter and other interventional devices and therapy delivery systems provides the means by which direct visualization and control can be achieved.

Turning now to the figures, FIG. 1 shows a catheter embodiment having an ultrasound transducer array 7 located on a deflectable distal end of the catheter 1. Specifically, catheter 1 comprises a proximal end 3 and a distal end 2. Located on the distal end 2 is the ultrasound transducer array 7. Attached to ultrasound transducer array 7 is at least one electrically conductive wire 4 (such as a microminiature flat cable) that extends from the array 7 to the proximal end 3 of catheter 1. The at least one electrically conductive wire 4 exits the catheter proximal end 3 through a port or other opening in the catheter wall and is connected to transducer driver; image processor 5 which provides a visual image via device 6.

Figure 2A:
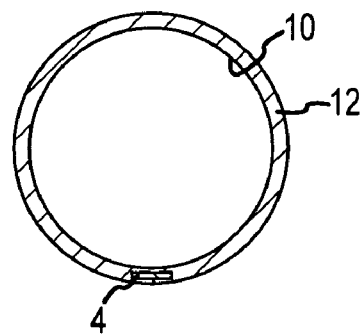
FIG. 2A shows a cross-sectional view of the catheter embodiment of FIG. 1.

FIG. 2A is a cross-section of FIG. 1 taken along lines A-A. As can be seen in FIG. 2A, the catheter 1 includes a catheter wall portion 12 that extends at least the length of proximal end 3 and further defines lumen 10 that extends at least the length of proximal end 3. Catheter wall 12 can be any suitable material or materials, such as extruded polymers, and can comprise one or more layers of materials. Further shown is the at least one electrically conductive wire 4 located at the bottom portion of wall 12.

Figure 2B:
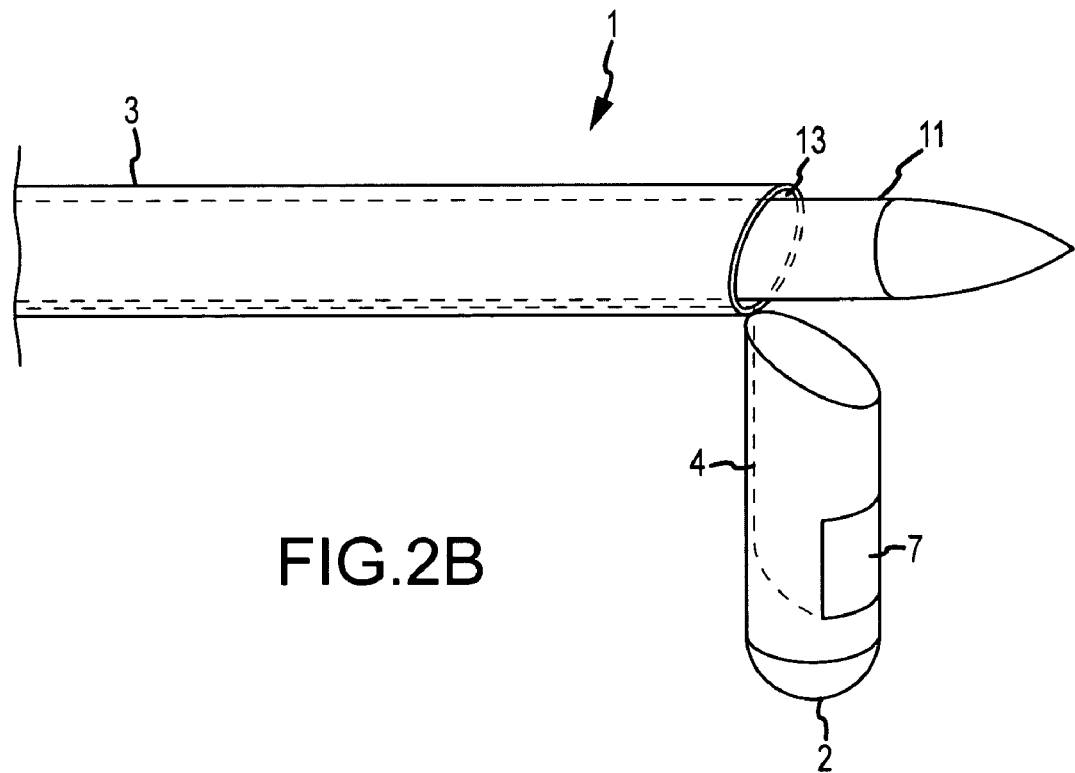
FIG. 2B shows a catheter embodiment having a deflectable ultrasound transducer array located at a distal end of the catheter.

Operation of the catheter 1 can be understood with reference to FIGS. 1 and 2B. Specifically, the catheter distal end 2 can be introduced into the desired body lumen and advanced to a desired treatment site with ultrasound transducer array 7 in a "side-looking" configuration (as shown in FIG. 1). Once the target area is reached, interventional device 11 can be advanced through the lumen 10 of the catheter 1 and out the distal port 13 and advanced in a distal direction. As can be seen, the catheter 1 can be configured such that advancing interventional device 11 in a distal direction out distal port 13 can deflect distal end 2 and thus result in ultrasound transducer array 7 being converted from "side-looking" to "forward-looking". Thus, the physician can advance interventional device 11 into the field of view of ultrasound transducer array 7.

"Deflectable" is defined as the ability to move the ultrasound transducer array, or a portion of the catheter body containing the ultrasound transducer array, away from the longitudinal axis of the catheter body, preferably such that 1) the transducer face is fully or partially forward facing, and 2) the distal exit port of the delivery lumen and the catheter body can be opened. Deflectable can include 1) "actively deflectable" meaning that the array or catheter portion containing the array can be moved by remote application of force (e.g., electrical (e.g., wired or wireless), mechanical, hydraulic, pneumatic, magnetic, etc.), transmission of that force by various means including pull wires, hydraulic lines, air lines, magnetic coupling, or electrical conductors; and 2) "passively deflectable" meaning that the array or catheter portion containing the array when in the resting, unstrained condition, tends to be in alignment with the catheter longitudinal axis and may be moved by local forces imparted by the introduction of interventional device 11.

Figure 2C:
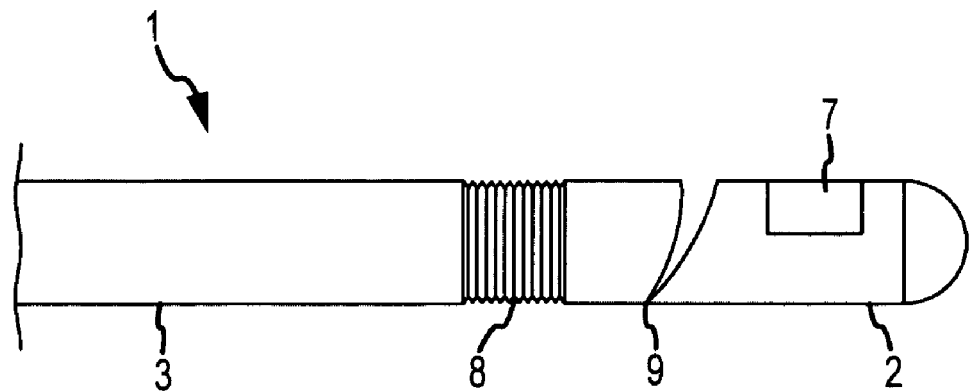
FIGS. 2C and 2D show the catheter embodiment of FIGS. 2A and 2B, wherein the catheter further includes an optional steerable segment.

In certain embodiments, the ultrasound transducer array may be deflected up to 90 degrees from the longitudinal axis of the catheter, as shown in FIG. 2B. Moreover, the deflectable ultrasound transducer array 7 can be attached to the catheter by a hinge 9 as shown in FIG. 2C. In an embodiment, hinge 9 can be a spring-loaded hinged device. Such a spring-loaded hinge can be actuated from the proximal end of the catheter by any suitable means. In an embodiment, the spring-loaded hinge is a shape memory alloy actuated by withdrawal of an outer sheath.

Figure 2D:
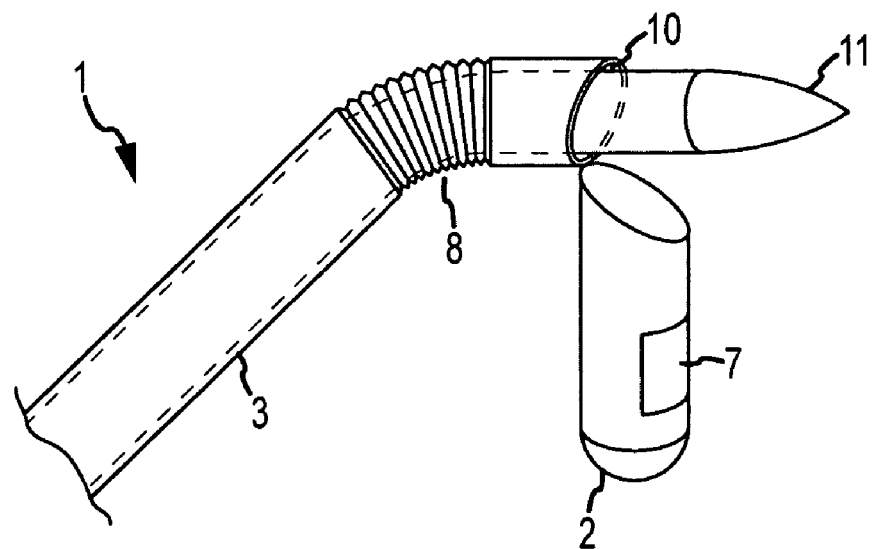

With reference to FIGS. 2C and 2D, the catheter 1 can further comprise a steerable segment 8. "Steerable" is defined as the ability to direct the orientation of the portions of the catheter 1 and lumen 10 distal to the steerable segment at an angle with respect to the catheter proximal to the steerable segment. FIG. 2D shows the steerable segment 8 deflected at an angle with respect to the catheter proximal to the steerable segment.

Figure 3A:
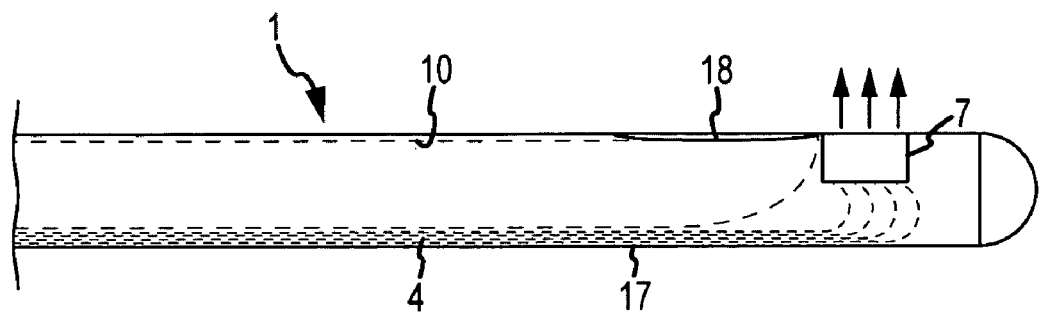
FIGS. 3A and 3B show a further catheter embodiment having a deflectable ultrasound transducer array located at a distal end of the catheter.
Figure 3B:
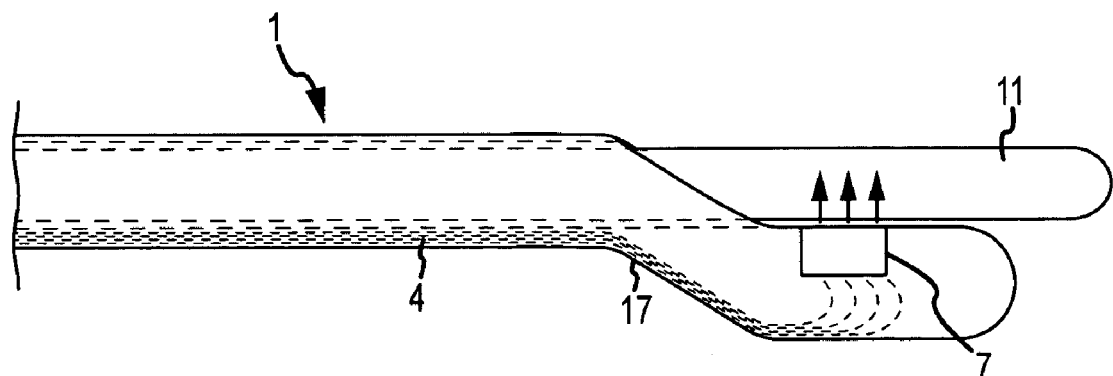

In a further embodiment, FIGS. 3A and 3B demonstrate a catheter 1 including an ultrasound transducer array 7 on a deflectable distal end 17 of the catheter 1. The catheter 1 comprises a proximal end (not shown) and a deflectable distal end 17. Ultrasound transducer array 7 is located at the deflectable distal end 17. Conductive wires 4 are attached to the ultrasound transducer array 7 and extend in a proximal direction to the proximal end of catheter 1. The catheter 1 also includes a generally centrally located lumen 10 that extends from the proximal end to the distal tip of the catheter. At distal end 17, the generally centrally located lumen 10 is essentially blocked or closed off by ultrasound transducer array 7. Finally, the catheter 1 also includes at least one longitudinally extending slit 18 that extends through a region proximal to the ultrasound transducer array 7.

As can be seen in FIG. 3B, once interventional device 11 is advanced distally through lumen 10, the interventional device 11 deflects deflectable distal end 17 and ultrasound transducer array 7 in a downward motion, thus opening lumen 10 so that interventional device 11 may be advanced distally past the ultrasound transducer array 7.

In various embodiments described herein, catheters may be provided having an ultrasound transducer array located near the distal end thereof. The catheter body may comprise a tube having a proximal end and a distal end. Moreover, the catheter may have at least one lumen extending from the proximal end to at least near the ultrasound transducer array. The catheter may comprise electrically conductive wires (e.g., a microminiature flat cable) attached to the ultrasound transducer array and being imbedded in the catheter wall and helically extending from the ultrasound transducer array to the proximal end of the catheter.

Figure 4:
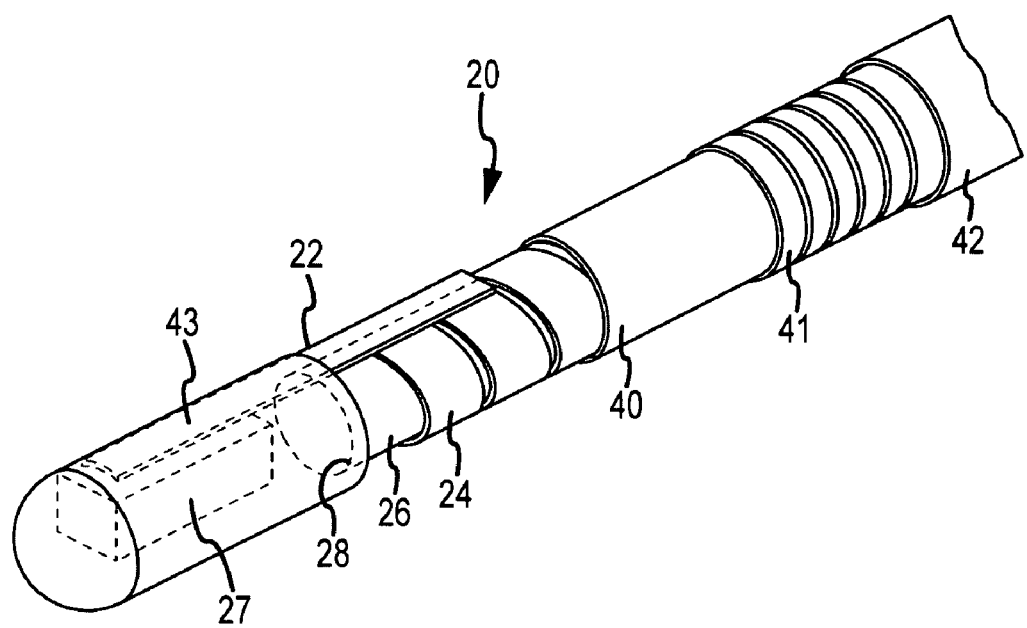
FIG. 4 shows a catheter embodiment having electrically conductive wires attached to an ultrasound transducer array located near the distal end of the catheter, wherein the electrically conductive wires helically extend to the proximal end of the catheter and are embedded in the catheter wall.
Figure 4A:
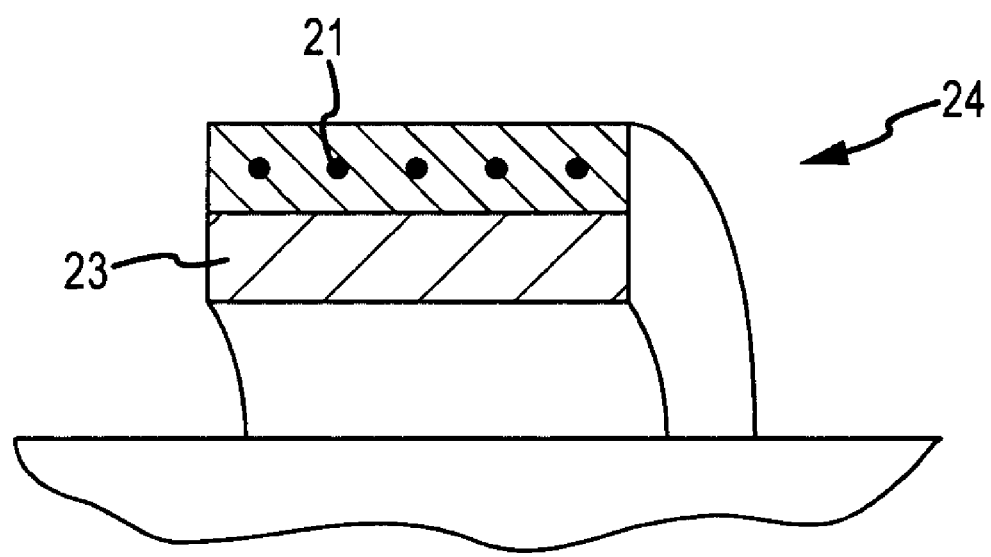
FIG. 4A shows an exemplary conductive wire assembly.

Such a catheter is depicted, for example, in FIGS. 4 and 4A. Specifically, FIGS. 4 and 4A demonstrate catheter 20 having a proximal end (not shown) and a distal end 22 with ultrasound transducer array 27 located at the distal end 22 of catheter 20. As can be seen, lumen 28 is defined by the inner surface of polymer tube 26, which can be formed from a suitable lubricious polymer (such as, for example, PEBAX® 72D, PEBAX® 63D, PEBAX® 55D, high density polyethylene, polytetrafluoroethylene, and expanded polytetrafluoroethylene, and combinations thereof) and extends from the proximal end to the distal end 22 near the ultrasound transducer array 27. The electrically conductive wires (e.g., microminiature flat cable) 24 are helically wrapped about polymer tube 26 and extend from near the ultrasound transducer array 27 proximally to the proximal end. An example of a suitable microminiature flat cable is shown in FIG. 4A where microminiature flat cable 24 includes electrically conductive wires 21 and suitable ground, such as copper 23. A conductive circuit element 43 (such as a flexboard) is attached to ultrasound transducer array 27 and to the electrically conductive wires 24. A suitable polymer film layer 40 (such as a lubricious polymer and or shrink wrap polymer) can be located over electrically conductive wires 24 to act as an insulating layer between the electrically conductive wires 24 and a shielding layer 41. Shielding layer 41 may comprise any suitable conductor that can be helically wrapped over polymer film 40, for example, in the opposing direction of the electrically conductive wires 21. Finally, outer jacket 42 can be provided over shielding layer 41 and can be of any suitable material, such as a lubricious polymer. Suitable polymers include, for example, PEBAX® 70D, PEBAX® 55D, PEBAX® 40D, and PEBAX® film 23D. The catheter depicted in FIGS. 4 and 4A can include the deflectable distal end and steerable segments discussed above.

The above catheter provides a means to electrically interface with an ultrasound probe at the distal end of a catheter while providing a working lumen to facilitate delivery of interventional devices to the imaged area. The construction of the catheter utilizes the conductors both to power the array as well as to provide mechanical properties that enhance kink resistance and torqueability. The novel construction presented provides a means to package the conductors and necessary shielding in a thin wall, thus providing a sheath profile that is suited for interventional procedures, with an OD targeted at or below 14 French (Fr) and an ID targeted at above 8 Fr, thus facilitating delivery of typical ablation catheters, filter delivery systems, needles, and other common interventional devices designed for vascular and other procedures.

Figure 5A:
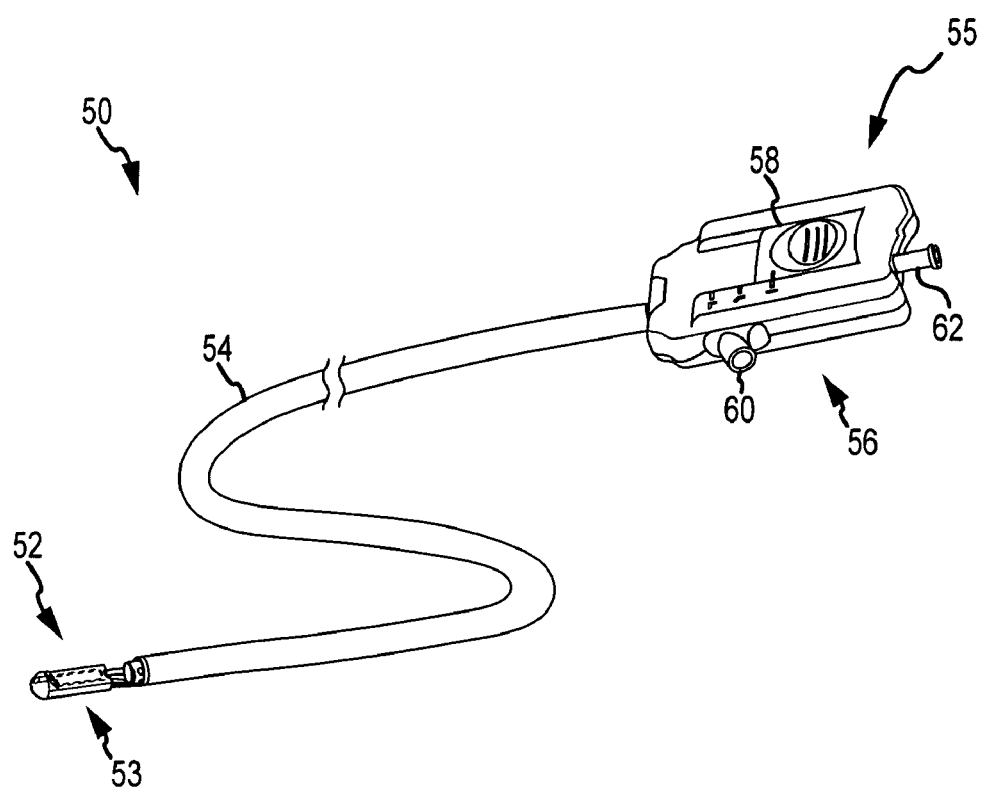
FIG. 5A shows an embodiment of a catheter that includes a deflectable member.

FIG. 5A shows an embodiment of a catheter 50 that includes a deflectable member 52 and a catheter body 54. The catheter body 54 may be flexible and capable of bending to follow the contours of a body vessel into which it is being inserted. The deflectable member 52 may be disposed at a distal end 53 of the catheter 50. The catheter 50 includes a handle 56 that may be disposed at a proximal end 55 of the catheter 50. During a procedure where the deflectable member 52 is inserted into the body of a patient, the handle 56 and a portion of the catheter body 54 remain outside of the body. The user (e.g., physician, technician, interventionalist) of the catheter 50 may control the position and various functions of the catheter 50. For example, the user may hold the handle 56 and manipulate a slide 58 to control a deflection of the deflectable member 52. In this regard, the deflectable member 52 may be selectively deflectable. The handle 56 and slide 58 may be configured such that the position of the slide 58 relative to the handle 56 may be maintained, thereby maintaining the selected deflection of the deflectable member 52. Such maintenance of position may at least partially be achieved by, for example, friction (e.g., friction between the slide 58 and a stationary portion of the handle 56), detents, and/or any other appropriate means. The catheter 50 may be removed from the body by pulling (e.g., pulling the handle 56).

Furthermore, the user may insert an interventional device (e.g., a diagnostic device and/or therapeutic device) through an interventional device inlet 62. The user may then feed the interventional device through the catheter 50 to move the interventional device to the distal end 53 of the catheter 50. Electrical interconnections between an image processor and the deflectable member may be routed through an electronics port 60 and through the catheter body 54 as described below.

FIGS. 5B through 5E show an embodiment of a catheter that includes a deflectable member 52 wherein the deflectable member 52 is deflectable by moving an inner tubular body 80 relative to an outer tubular body 79 of the catheter body 54. As shown in FIG. 5B, the illustrated deflectable member 52 includes a tip 64. The tip 64 may encase various components and members.

The tip 64 may have a cross section that corresponds to the cross section of the outer tubular body 79. For example, and as illustrated in FIG. 5B, the tip 64 may have a rounded distal end 66 that corresponds to the outer surface of the outer tubular body 79. The portion of the tip 64 that houses the ultrasound transducer array 68 may be shaped to at least partially correspond (e.g., along the lower outer surface of the tip 64 as viewed in FIG. 5B) to the outer surface of the outer tubular body 79. At least a portion of the tip 64 may be shaped to promote transport through internal structures of the patient such as the vasculature. In this regard, the rounded distal end 66 that may aid in moving the deflectable member 52 through the vasculature. Other appropriate end shapes may be used for the shape of the distal end 66 of the tip 64.

Figure 5C:
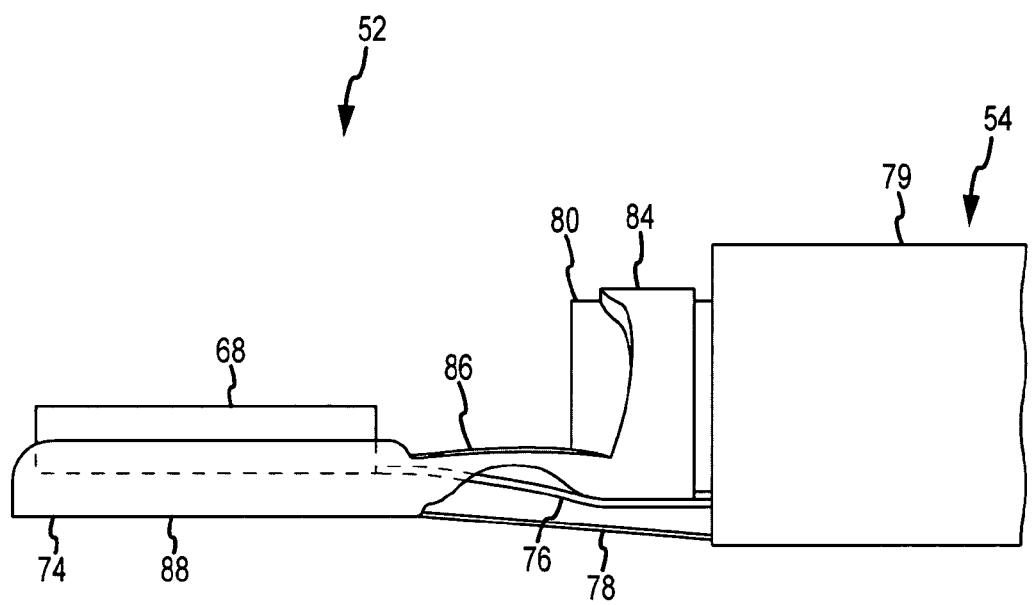
Figure 5D:
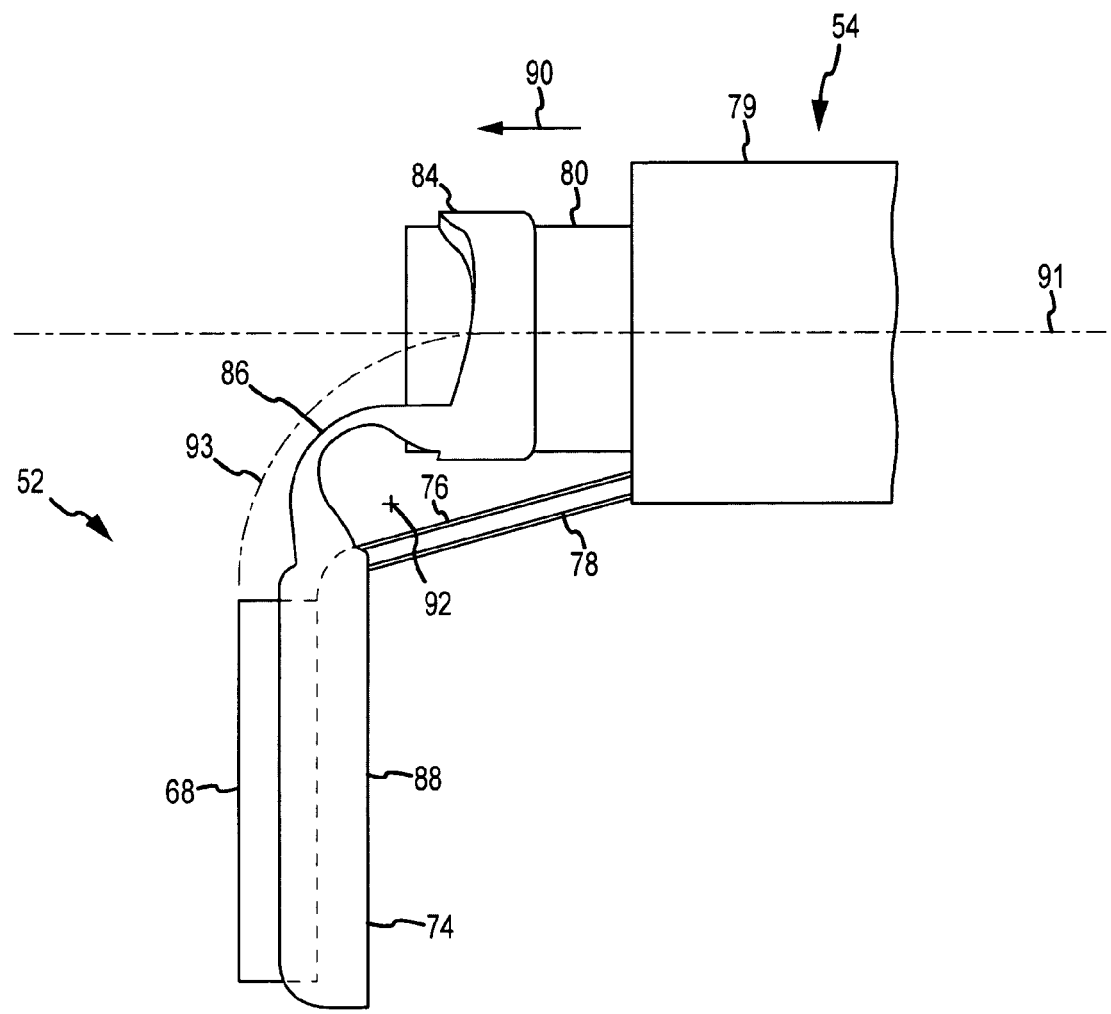

In an embodiment, such as the one illustrated in FIGS. 5B through 5D, the tip 64 may hold an ultrasound transducer array 68. As will be appreciated, as illustrated in FIG. 5B, the ultrasound transducer array 68 may be side-looking when the deflectable member 52 is aligned with the outer tubular body 79. The field of view of the ultrasound transducer array 68 may be located perpendicular to the flat upper face (as oriented in FIG. 5B) of the ultrasound transducer array 68. As illustrated in FIG. 5B, the field of view of the ultrasound transducer array 68 may be unobstructed by the outer tubular body 79 when the ultrasound transducer array 68 is side-looking. In this regard, the ultrasound transducer array 68 may be operable to image during catheter body 54 positioning, thereby enabling imaging of anatomical landmarks to aid in positioning the distal end of a lumen 82. The ultrasound transducer array 68 may have an aperture length. The aperture length may be greater than a maximum cross dimension of the outer tubular body 79. At least a portion of the deflectable member 52 may be permanently positioned distal to the distal end of the outer tubular body 79. In an embodiment, the entirety of the deflectable member 52 may be permanently positioned distal to the distal end of the outer tubular body 79. In such an embodiment, the deflectable member may be incapable of being positioned within the outer tubular body 79.

The tip 64 may further include a feature to enable the catheter to follow a guide wire. For example, as illustrated in FIG. 5B, the tip 64 may include a distal guide wire aperture 70 functionally connected to a proximal guide wire aperture 72. In this regard, the catheter may be operable to travel along the length of a guide wire threaded through the distal 70 and proximal 72 guide wire apertures.

As noted, the deflectable member 52 may be deflectable relative to the outer tubular body 79. In this regard, the deflectable member 52 may be interconnected to one or more members to control the motion of the deflectable member 52 as it is being deflected. A tether 78 may interconnect the deflectable member 52 to the catheter body 54. The tether 78 may be anchored to the deflectable member 52 on one end and to the catheter body 54 on the other end. The tether 78 may be configured as a tensile member operable to prevent the anchor points from moving a distance away from each other greater than the length of the tether 78. In this regard, through the tether 78, the deflectable member 52 may be restrainably interconnected to the outer tubular body 79.

An inner tubular body 80 may be disposed within the outer tubular body 79. The inner tubular body 80 may include the lumen 82 passing through the length of the inner tubular body 80. The inner tubular body 80 may be movable relative to the outer tubular body 79. This movement may be actuated by movement of the slide 58 of FIG. 5A. A support 74 may interconnect the deflectable member 52 to the inner tubular body 80. The support 74 may be structurally separate from the inner tubular body 80 and the outer tubular body 79. A flexboard 76 may contain electrical interconnections operable to electrically connect the ultrasound transducer array 68 to an electrical interconnection member 104 (shown in FIG. 5E) disposed within the outer tubular body 79. The exposed portion of flexboard 76 between the tip 64 and the outer tubular body 79 may be encapsulated to isolate it from possible contact with fluids (e.g., blood) when the deflectable member 52 is disposed within a patient. In this regard, the flexboard 76 may be encapsulated with an adhesive, a film wrap, or any appropriate component operable to isolate the electrical conductors of the flexboard 76 from the surrounding environment. In an embodiment, the tether 78 may be wrapped around the portion of the flexboard 76 between the tip 64 and the outer tubular body 79.

Deflection of the deflectable member 52 will now be discussed with reference to FIGS. 5C and 5D. FIGS. 5C and 5D illustrate the deflectable member 52 with the portion of the tip 64 surrounding the ultrasound image array 68 and support 74 removed. As illustrated in FIG. 5C, the support 74 may include a tubular body interface portion 84 operable to fix the support 74 to the inner tubular body 80. The tubular body interface portion 84 may be fixed to the inner tubular body 80 in any appropriate manner. For example, the tubular body interface portion 84 may be secured to the inner tubular body 80 with an external shrink wrap. In such a configuration, the tubular body interface portion 84 may be placed over the inner tubular body 80 and then a shrink-wrap member may be placed over the tubular body interface portion 84. Heat may then be applied causing the shrink wrap material to shrink and fix the tubular body interface portion 84 to the inner tubular body 80. An additional wrap may then be applied over the shrink wrap to further fix the tubular body interface portion 84 to the inner tubular body 80. In another example, the tubular body interface portion 84 may be secured to the inner tubular body 80 with an adhesive, a weld, fasteners, or any combination thereof.

The support 74 may comprise, for example, a shape memory material (e.g., a shape memory alloy such as Nitinol). The support 74 may further include a hinge portion 86. The hinge portion 86 may comprise one or more members interconnecting the tubular body interface portion 84 with a cradle portion 88. The hinge portion 86, as illustrated in FIGS. 5B through 5C, may comprise two members. The cradle portion 88 may support the ultrasound transducer array 68. The support 74, including the hinge portion 86, may possess a column strength adequate to keep the deflectable member 52 substantially aligned with the outer tubular body 79 in the absence of any advancement of the inner tubular body 80 relative to the outer tubular body 79. In this regard, the deflectable member 52 may be operable to remain substantially aligned with the outer tubular body 79 when the outer tubular body 79 is being inserted into and guided through the patient.

The hinge portion 86 may be shaped such that upon application of an actuation force, the hinge portion 86 elastically deforms along a predetermined path about a deflection axis 92. The predetermined path may be such that the tip 64 and the hinge portion 86 each are moved to a position where they do not interfere with an interventional device emerging from the distal end of the lumen 82. An imaging field of view of the ultrasound transducer array 68 may be substantially maintained in a position relative to the outer tubular body 79 when the interventional device is advanced through the exit port 81 at the distal end of the lumen 82 and into the field of view. As illustrated in FIGS. 5B through 5D, the hinge portion may comprise two generally parallel sections 86*a* and 86*b,* where the ends of each of the generally parallel sections 86*a* and 86*b* (e.g., where the hinge portion 86 meets the cradle portion 88 and where the hinge portion 86 meets the tubular body interface portion 84) may be generally shaped to coincide with a cylinder oriented along a center axis 91 of the inner tubular body 80. A central portion of each of the generally parallel sections 86*a* and 86*b* may be twisted toward the center axis 91 of the outer tubular body 79 such that the central portions are generally aligned with the deflection axis 92. The hinge portion 86 is disposed such that it is disposed about less than the entirety of the circumference of the inner tubular body 80.

To deflect the deflectable member 52 relative to the outer tubular body 79, the inner tubular body 80 may be moved relative to the outer tubular body 79. Such relative movement is illustrated in FIG. 5D. As shown in FIG. 5D, movement of the inner tubular body 80 in an actuation direction 90 (e.g., in the direction of the ultrasound transducer array 68 when the deflectable member 52 is aligned with the outer tubular body 79) may impart a force on the support 74 in the actuation direction 90. However, since the cradle portion 88 is restrainably connected to the outer tubular body 79 by the tether 78, the cradle portion 88 is prevented from moving substantially in the actuation direction 90. In this regard, the movement of the inner tubular body 80 in the actuation direction 90 may result in the cradle portion 88 pivoting about its interface with the tether 78 and also in the hinge portion 86 bending as illustrated in FIG. 5D. Thus the movement of the inner tubular body 80 in the actuation direction 90 may result in the cradle portion 88 (and the ultrasound transducer array 68 attached to the cradle portion 80) rotating 90 degrees as illustrated in FIG. 5D. Accordingly, movement of the inner tubular body 80 may cause a controlled deflection of the deflectable member 52. As illustrated, the deflectable member 52 may be selectively deflectable away from the center axis 91 of the outer tubular body 79.

In an exemplary embodiment, a movement of the inner tubular body 80 of about 0.1 cm may result in the deflectable member 52 deflecting through an arc of about 9 degrees. In this regard, movement of the inner tubular body 80 of about 1 cm may result in the deflectable member 52 deflecting about 90 degrees. Thusly, the deflectable member 52 may be selectively deflected from a side-looking position to a forward-looking position. Intermediate positions of the deflectable member 52 may be achieved by moving the inner tubular body 80 a predeterminable distance. For example, in the current exemplary embodiment, the deflectable member 52 may be deflected 45 degrees from the side-looking position by moving the inner tubular body 80 about 0.5 cm relative to the outer tubular body 79 in the actuation direction 90. Other appropriate member geometries may be incorporated to produce other relationships between inner tubular body 80 and deflectable member 52 deflection. Moreover, deflections of greater than 90 degrees may be obtained. Moreover, an embodiment of the catheter 50 may be configured such that a predeterminable maximum deflection of the deflectable member 52 may be achieved. For example, the handle 56 may be configured to limit the movement of the slide 58 such that the full range of movement of the slide 58 corresponds to a 45 degree deflection (or any other appropriate deflection) of the deflectable member 52.

The slide 58 and handle 56 may be configured such that substantially any relative motion of the slide 58 to the handle 56 results in a deflection of the deflectable member 52. In this regard, there may be substantially no dead zone of the slide 58 where slide 58 movement does not result in deflection of the deflectable member 52. Furthermore, the relationship between movement of the slide 58 (e.g., relative to the handle 56) and the amount of corresponding deflection of the deflectable member 52 may be substantially linear.

When the deflectable member 52 is deflected from the position illustrated in FIG. 5C so that no part of the tip 64 occupies a cylinder the same diameter as and extending distally from the exit port 81, an interventional device may be advanced through the exit port 81 without contacting the tip 64. As such, the imaging field of view of the ultrasound transducer array 68 may be maintained in a fixed registration relative to the catheter body 54 while the interventional device is being advanced into the catheter body 54, through the exit port 81, and into the imaging field of view of the ultrasound transducer array 68.

When in a forward-looking position, the field of view of the ultrasound transducer array 68 may encompass an area in which an interventional device may be inserted through the lumen 82. In this regard, the ultrasound transducer array 68 may be operable to aid in the positioning and operation of the interventional device.

The deflectable member 52 may deflect about the deflection axis 92 (deflection axis 92 is aligned with the view of FIG. 5D and therefore is represented by a point). The deflection axis 92 may be defined as a point fixed relative to the tubular body interface portion 84 about which the cradle portion 88 rotates. As illustrated in FIG. 5D, the deflection axis 92 may be offset from the center axis 91 of the outer tubular body 79. For any given deflection of the deflectable member 52, a displacement arc 93 may be defined as the minimum arc that is tangent to a face of the deflectable member 52 and tangent the center axis 91 of the catheter. In an embodiment of the catheter 50, the ratio of a maximum cross-dimension of the distal end of the outer tubular body 79 to the radius of the displacement arc 93 may be at least about 1.

The deflectable member 52 may deflect about the deflection axis 92 such that the ultrasound transducer array 68 is positioned proximate to the exit port 81. Such positioning, in conjunction with a small displacement arc 93, reduces the distance an interventional device must travel between emerging from the exit port 81 and entering the field of view of the ultrasound transducer array 68. For example, upon deflection of 90 degrees as shown in FIG. 5D, the ultrasound transducer array 68 may be positioned such that the acoustical face of the ultrasound transducer array 68 is a distance from the exit port 81 (as measured along the central axis 91) that is less than the maximum cross dimension of the distal end of the outer tubular body 79.

As illustrated in FIGS. 5C and 5D, the flexboard 76 may remain interconnected to the catheter body 54 and the deflectable member 52 independent of the deflection of the deflectable member 52.

Figure 5E:
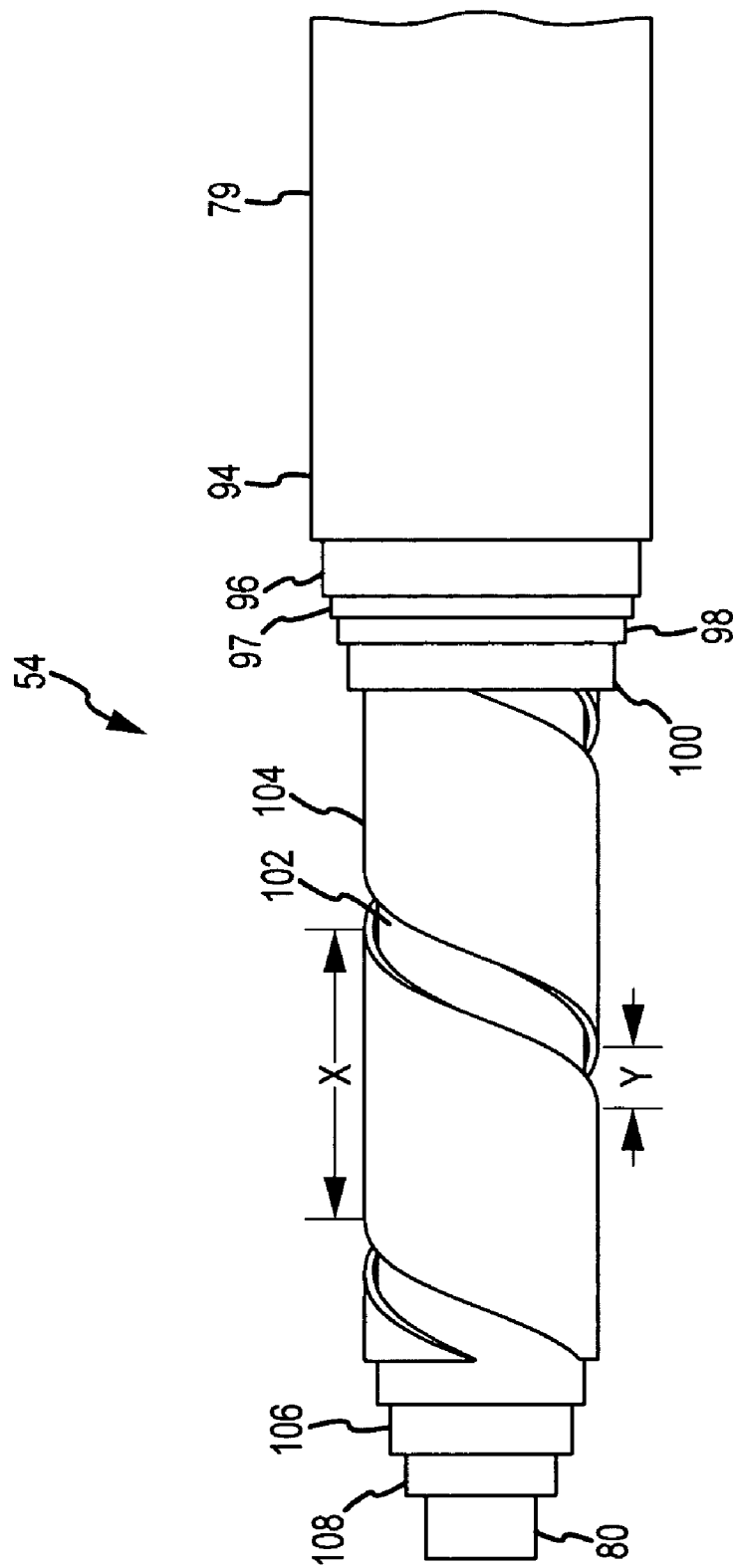

FIG. 5E illustrates an embodiment of the catheter body 54. The catheter body 54 as illustrated comprises the inner tubular body 80 and the outer tubular body 79. In the illustrated embodiment, the outer tubular body 79 comprises all of the components illustrated in FIG. 5E except for the inner tubular body 80. For the illustration of FIG. 5E, portions of various layers have been removed to reveal the construction of the catheter body 54. The outer tubular body 79 may include an outer covering 94. The outer covering 94 may, for example, be a high voltage breakdown material. In an exemplary configuration the outer covering 94 may comprise a substantially non-porous composite film including expanded polytetrafluoroethylene (ePTFE) with a thermal adhesive layer of ethylene fluoroethylene perfluoride on one side. The exemplary configuration may have a width of about 25 mm, a thickness of about 0.0025 mm, an isopropyl alcohol bubble point of greater than about 0.6 MPa, and a tensile strength of about 309 MPa in the length direction (e.g., the strongest direction). The outer covering 94 may be lubricious to aid in the passage of the outer tubular body 79 through the patient. The outer covering 94 may provide a high voltage breakdown. Within the outer covering 94 may be disposed an outer low-dielectric constant layer 96. The outer low-dielectric constant layer 96 may reduce capacitance between the electrical interconnection member 104 and materials (e.g., blood) outside of the outer covering 94. The outer low-dielectric constant layer 96 may have a dielectric constant of less than about 2.2. In an embodiment, the outer low-dielectric constant layer 96 may be about 0.07-0.15 mm thick. In an embodiment, the outer low-dielectric constant layer 96 may comprise a porous material, such as ePTFE. The voids in the porous material may be filled with a low-dielectric material such as air.

Moving toward the center of the outer tubular body 79, the next layer may be first tie layer 97. The first tie layer 97 may comprise a film material that may have a melt temperature that is lower then other components of the outer tubular body 79. During fabrication of the outer tubular body 79, the first tie layer 100 may be selectively melted to yield an interconnected structure. For example, selectively melting the first tie layer 97 may serve to secure the outer low-dielectric constant layer 96, the first tie layer 97, and a shield layer 98 (discussed below) to each other.

Moving toward the center of the outer tubular body 79, the next layer may be the shield layer 98. The shield layer 98 may be used to reduce electrical emissions from the outer tubular body 79. The shield layer 98 may be used to shield components internal to the shield layer 98 (e.g., the electrical interconnection member 104) from external electrical noise. The shield layer 98 may be in the form of a double served wire shield or braid. In an exemplary embodiment, the shield layer 98 may be about 0.05-0.08 mm thick. Moving toward the center of the outer tubular body 79, the next layer may be a second tie layer 100. The second tie layer 100 may comprise a film material that may have a melt temperature that is lower then other components of the outer tubular body 79. During fabrication of the outer tubular body 79, the second tie layer 100 may be selectively melted to yield an interconnected structure.

Interior to the second tie layer 100 may be the electrical interconnection member 104. The electrical interconnection member 104 may comprise a plurality of conductors arranged in a side-by-side fashion with an insulative (e.g., non-conductive) material between the conductors. The electrical interconnection member 104 may comprise one or more microminiature flat cables. The electrical interconnection member 104 may contain any appropriate number of conductors arranged in a side-by-side fashion. By way of example, the electrical interconnection member 104 may contain 32 or 64 conductors arranged in a side-by-side fashion. The electrical interconnection member 104 may be helically disposed within the outer tubular body 79. In this regard, the electrical interconnection member 104 may be helically disposed within the wall of the outer tubular body 79. The electrical interconnection member 104 may be helically disposed such that no part of the electrical interconnection member 104 overlies itself. The electrical interconnection member 104 may extend from the proximal end 55 of the catheter 50 to the distal end 53 of the outer tubular body 79. In an embodiment, the electrical interconnection member 104 may be disposed parallel to and along the center axis of the outer tubular body 79.

As illustrated in FIG. 5E, there may be a gap of width Y between the coils of the helically wound electrical interconnection member 104. In addition, the electrical interconnection member 104 may have a width of X as illustrated in FIG. 5E. The electrical interconnection member 104 may be helically disposed such that the ratio of the width X to the width Y is greater than 1. In such an arrangement, the helically disposed electrical interconnection member 104 may provide significant mechanical strength to the outer tubular body 79. This may, in certain embodiments, obviate or reduce the need for a separate reinforcing layer within the outer tubular body 79. Moreover, the gap Y may vary along the length of the outer tubular body 79 (e.g., continuously or in one or more discrete steps). For example, it may be beneficial to have a greater stiffness to the outer tubular body 79 toward the proximal end of the outer tubular body 79. Accordingly, the gap Y may be made smaller toward the proximal end of the outer tubular body 79.

An inner tie layer 102 may be disposed interior to the electrical interconnection member 104. The inner tie layer 102 may be configured similar to and serve a similar function as the second tie layer 100. The inner tie layer 102 may have a melting point of, for example, 160 degrees Celsius. Moving toward the center of the outer tubular body 79, the next layer may be an inner low-dielectric constant layer 106. The inner low-dielectric constant layer 106 may be configured similar to and serve a similar function as the outer low-dielectric constant layer 96. The inner low-dielectric constant layer 106 may be operable to reduce capacitance between the electrical interconnection member 104 and materials (e.g., blood, interventional device) within the outer tubular body 79. Moving toward the center of the outer tubular body 79, the next layer may be an inner covering 108. The inner covering 108 may be configured similar to and serve a similar function as the outer covering 94.

The tie layers (first tie layer 97, second tie layer 100, and inner tie layer 102) may each have substantially the same melting point. In this regard, during construction, the catheter body 54 may be subjected to an elevated temperature that may melt each of the tie layers simultaneously and fix various layers of the catheter body 54 relative to each other. Alternatively, the tie layers may have different melting points allowing selective melting of one or two of the tie layers while leaving the other tie layer or tie layers unmelted. Accordingly, embodiments of catheter bodies 54 may comprise zero, one, two, three, or more tie layers that have been melted to secure various layers of the catheter body 54 to other layers of the catheter body 54.

The aforementioned layers (from the outer covering 94 through the inner covering 108) may each be fixed relative to each other. Together these layers may form the outer tubular body 79. Interior to these layers and movable relative to these layers may be the inner tubular body 80. The inner tubular body 80 may be disposed such that there is an amount of clearance between the outside surface of the inner tubular body 80 and the interior surface of the inner covering 108. The inner tubular body 80 may be a braid reinforced polyether block amide (e.g., the polyether block amide may comprise a PEBAX® material available from Arkema Inc. Philadelphia, Pa.) tube. The inner tubular body 80 may be reinforced with a braided or coiled reinforcing member. The inner tubular body 80 may possess a column strength adequate that it may be capable of translating a lateral motion of the slide 58 along the length of the inner tubular body 80 such that the deflectable member 52 may be actuated by the relative movement of the inner tubular body 80 where its interfaces with the support 74. The inner tubular body 80 may also be operable to maintain the shape of the lumen 82 passing through the length of the inner tubular body 80 during deflection of the deflectable member 52. Accordingly, a user of the catheter 50 may be capable of selecting and controlling the amount of deflection of the deflectable member 52 through manipulation of the handle 56. The lumen 82 may have a center axis aligned with the center axis 91 of the outer tubular body 79.

In a variation of the embodiment illustrated in FIG. 5E, the inner tubular body 80 may be replaced with an external tubular body that is disposed outside of the outer covering 94. In such an embodiment, the components of the outer tubular body 79 (from the outer covering 94 to the inner covering 108) may remain substantially unchanged from as illustrated in FIG. 5E (the diameters of the components may be reduced slightly to maintain similar overall inner and outer diameters of the catheter body 54). The external tubular body may be fitted outside of the outer covering 94 and may be movable relative to the outer covering 94. Such relative movement may facilitate deflection of the deflectable member 52 in a manner similar to as described with reference to FIGS. 5A through 5D. In such an embodiment, the electrical interconnection member 104 would be a part of the outer tubular body 79 that would be located inside of the external tubular body. The external tubular body may be constructed similarly to the inner tubular body 80 described above.

In an exemplary embodiment, the catheter body 54 may have a capacitance of less than 2,000 picofarads. In an embodiment, the catheter body 54 may have a capacitance of about 1,600 picofarads. In the above-described embodiment of FIG. 5E, the outer covering 94 and outer low-dielectric constant layer 96 may, in combination, have a withstand voltage of at least about 2,500 volts AC. Similarly, the outer covering 108 and inner low-dielectric constant layer 106 may, in combination, have a withstand voltage of at least about 2,500 volts AC. Other embodiments may achieve different withstand voltages by, for example, varying the thicknesses of the covering and/or low-dielectric constant layers. In an exemplary embodiment, the outer diameter of the outer tubular body 79 may, for example, be about 12.25 Fr. The inner diameter of the inner tubular body may, for example, be about 8.4 Fr.

The catheter body 54 may have a kink diameter (the diameter of bend in the catheter body 54 below which the catheter body 54 will kink) that is less than ten times the diameter of the catheter body 54. Such a configuration is appropriate for anatomical placement of the catheter body 54.

As used herein, the term "outer tubular body" refers to the outermost layer of a catheter body and all layers of that catheter body disposed to move with the outermost layer. For example, in the catheter body 54 as illustrated in FIG. 5E, the outer tubular body 79 includes all illustrated layers of the catheter body 54 except the inner tubular body 80. Generally, in embodiments where there is no inner tubular body present, the outer tubular body may coincide with the catheter body.

Figure 5F:
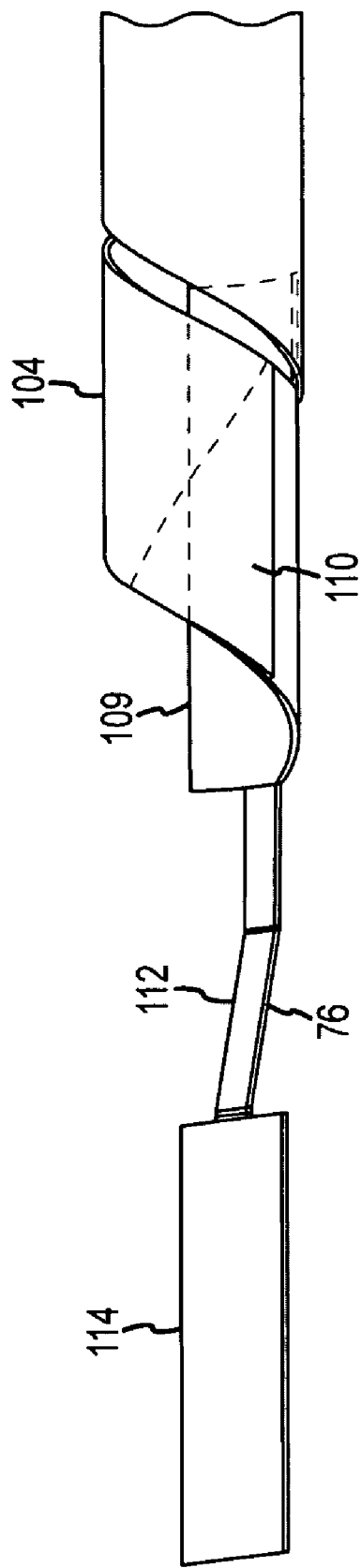
FIG. 5F shows an embodiment of an electrical interconnection between a helically disposed electrical interconnection member and a flexible electrical member.

FIG. 5F shows an embodiment of an electrical interconnection between the helically disposed electrical interconnection member 104 and the flexboard 76 (a flexible/bendable electrical member). For explanatory purposes, all the parts of the catheter body 54 except the electrical interconnection member 104 and the flexboard 76 are not illustrated in FIG. 5F. The flexboard 76 may have a curved section 109. The curved section 109 may be curved to correspond with the curvature of the outer tubular body 79. The curved section 109 of the flexboard 76 may be disposed within the outer tubular body 79 at the end of the outer tubular body 79 proximate to the deflectable member 52 in the same position with respect to the layers of the outer tubular body 79 as the electrical interconnection member 104. Accordingly, the curved section 109 of the flexboard 76 may come into contact with the electrical interconnection member 104. In this regard, the distal end of the electrical interconnection member 104 may interconnect to the flexboard 76 in an interconnect region 110.

Within the interconnect region 110, the electrically conductive portions (e.g., wires) of the electrical interconnection member 104 may be interconnected to electrically conductive portions (e.g., traces, conductive paths) of the flexboard 76. This electrical interconnection may be achieved by peeling back or removing some of the insulative material of the electrical interconnection member 104 and contacting the exposed electrically conductive portions to corresponding exposed electrically conductive portions on the flexboard 76. The end of the electrical interconnection member 104 and the exposed conductive portions of the electrical interconnection member 104 may be disposed at an angle relative to the width of the electrical interconnection member 104. In this regard, the pitch (e.g., the distance between exposed electrically conductive portions) between the exposed electrically conductive portions of the flexboard 76 may be greater than the pitch (as measured across the width) of the electrical interconnection member 104, while maintaining an electrical interconnection between each conductor of both the electrical interconnection member 104 and the flexboard 76.

As illustrated in FIG. 5F, the flexboard 76 may comprise a flexing or bending region 112 that has a width narrower than the width of the electrical interconnection member 104. As will be appreciated, the width of each individual electrically conductive path through the flexing region 112 may be smaller than the width of each electrically conductive member within the electrical interconnection member 104. Furthermore the pitch between each electrically conductive member within the flexing region 112 may be smaller than the pitch of the electrical interconnection member 104.

The flexing region 112 may be interconnected to an array interface region 114 of the flexboard 76 through which the electrically conductive paths of the electrical interconnection member 104 and the flexboard 76 may be electrically interconnected to individual transducers of the ultrasound transducer array 68.

As illustrated in FIGS. 5C and 5D, the flexing region 112 of the flexboard 76 may be operable to flex during deflection of the deflectable member 52. In this regard, the flexing region 112 may be bendable in response to deflection of the deflectable member 52. The individual conductors of the electrical interconnection member 104 may remain in electrical communication with the individual transducers of the ultrasound transducer array 68 during deflection of the deflectable member 52.

In an embodiment, the electrical interconnection member 104 may comprises two or more separate sets of conductors (e.g., two or more microminiature flat cables). In such an embodiment, each of the separate sets of conductors may be interconnected to the flexboard 76 in a manner similar to as illustrated in FIG. 5F. Furthermore, the electrical interconnection member 104 (either a unitary electrical interconnection member 104 as illustrated in FIG. 5F or an electrical interconnection member 104 comprising a plurality of generally parallel distinct cables) may comprise members that extend from the distal end 53 to the proximal end 55 of the catheter body 54 or the electrical interconnection member 104 may comprise a plurality of discrete, serially interconnected members that together extend from the distal end 53 to the proximal end 55 of the catheter body 54. In an embodiment, the flexboard 76 may include the electrical interconnection member 104. In such an embodiment, the flexboard 76 may have a helically wrapped portion extending from the distal end 53 to the proximal end 55 of the catheter body 54. In such an embodiment, no electrical conductor interconnections (e.g., between the flexboard 76 and a microminiature flat cable)) may be required between the array interface region 114 and the proximal end of the catheter body 54.

FIGS. 6A through 6D show an embodiment of a catheter that includes a deflectable member 116 wherein the deflectable member 116 is deflectable by moving an elongate member relative to an outer tubular body 118. It will be appreciated that the embodiment illustrated in FIGS. 6A through 6D does not include an inner tubular body and the outer tubular body 118 may also be characterized as a catheter body.

Figure 6A:
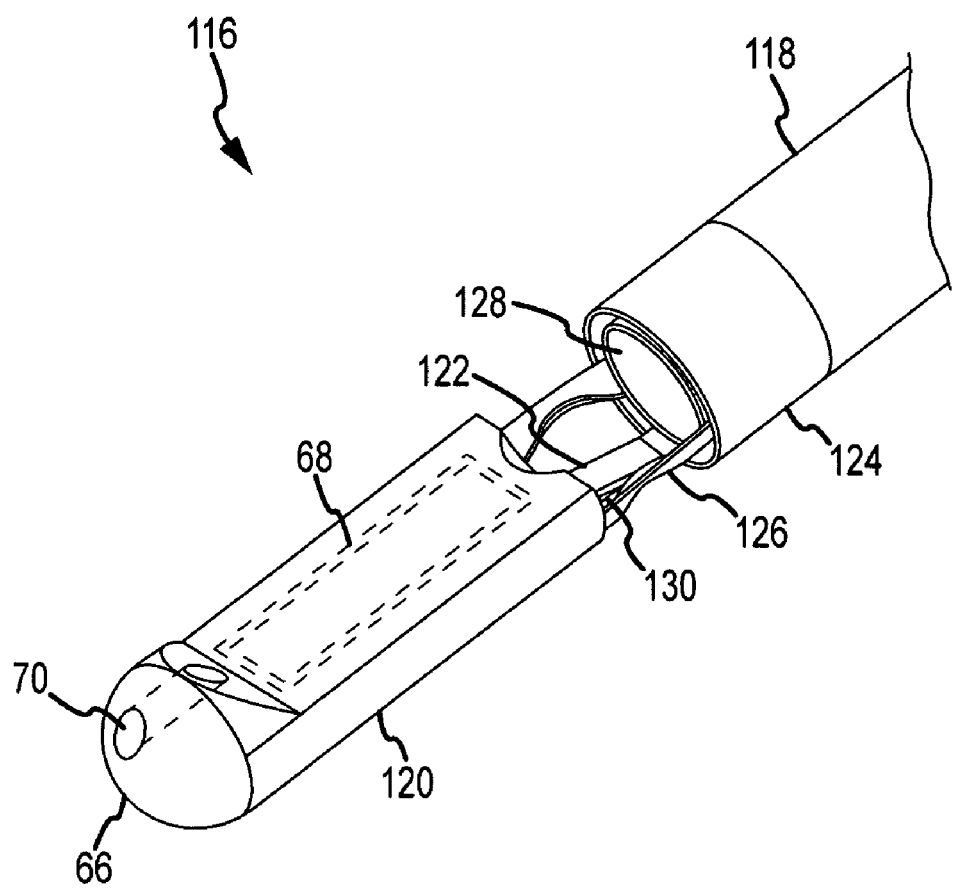
FIGS. 6A through 6D show an embodiment of a catheter that includes a deflectable member wherein the deflectable member is deflectable by moving an elongate member relative to a catheter body.

The deflectable member 116 may be selectively deflectable. As shown in FIG. 6A, the illustrated deflectable member 116 includes a tip 120. The tip 120 may include the ultrasound transducer array 68 and may include a rounded distal end 66 and guide wire aperture 70 similar to the tip 64 described with reference to FIG. 5B. As with the tip 64 of FIG. 5B, the ultrasound transducer array 68 may be side-looking when the deflectable member 116 is aligned with the outer tubular body 118. In this regard, the ultrasound transducer array 68 may be operable to image anatomical landmarks during catheter insertion to aid in guiding and/or positioning the outer tubular body 118.

The outer tubular body 118 may include a lumen 128 operable to allow an interventional device to pass therethrough. At least a portion of the deflectable member 116 may be permanently positioned distal to the distal end of with the outer tubular body 118. In an embodiment, the entirety of the deflectable member 116 may be permanently positioned distal to the distal end of the outer tubular body 118.

The deflectable member 116 may be deflectable relative to the outer tubular body 118. In this regard, the deflectable member 116 may be interconnected to one or more elongate members to control the motion of the deflectable member 116 as it is being deflected. The elongate member may take the form of a pull wire 130. The pull wire 130 may be a round wire. Alternatively, for example, the pull wire 130 may be rectangular in cross-section. For example, the pull wire may be rectangular in cross-section with a width-to-thickness ratio of about 5 to 1.

As with the catheter embodiment illustrated in FIGS. 5B through 5E, the catheter of FIGS. 6A through 6D may include a support 126 that supports the ultrasound transducer array 68. The support 126 may interconnect the deflectable member 116 to the outer tubular body 118. A flexboard 122 may contain electrical interconnections operable to electrically connect the ultrasound transducer array 68 to an electrical interconnection member 104 (shown in FIG. 6D) disposed within the outer tubular body 118. The exposed portion of flexboard 122 may be encapsulated similarly to the flexboard 76 discussed above.

The outer tubular body 118 may include a distal portion 124. The distal portion 124 may comprise a plurality of wrapped layers disposed about a securement portion 133 (shown in FIGS. 6B and 6C) of the support 126. The wrapped layers may serve to secure the securement portion 133 to an inner portion of the outer tubular body 118 as discussed below with reference to FIG. 6D.

Figure 6B:
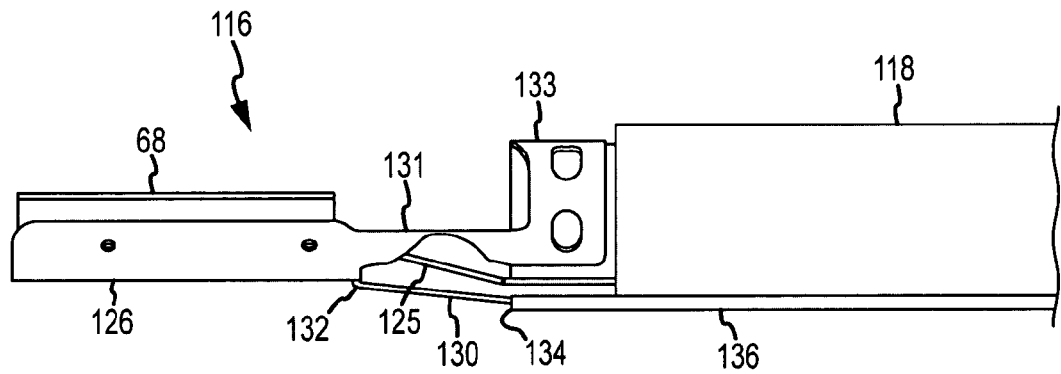
Figure 6C:
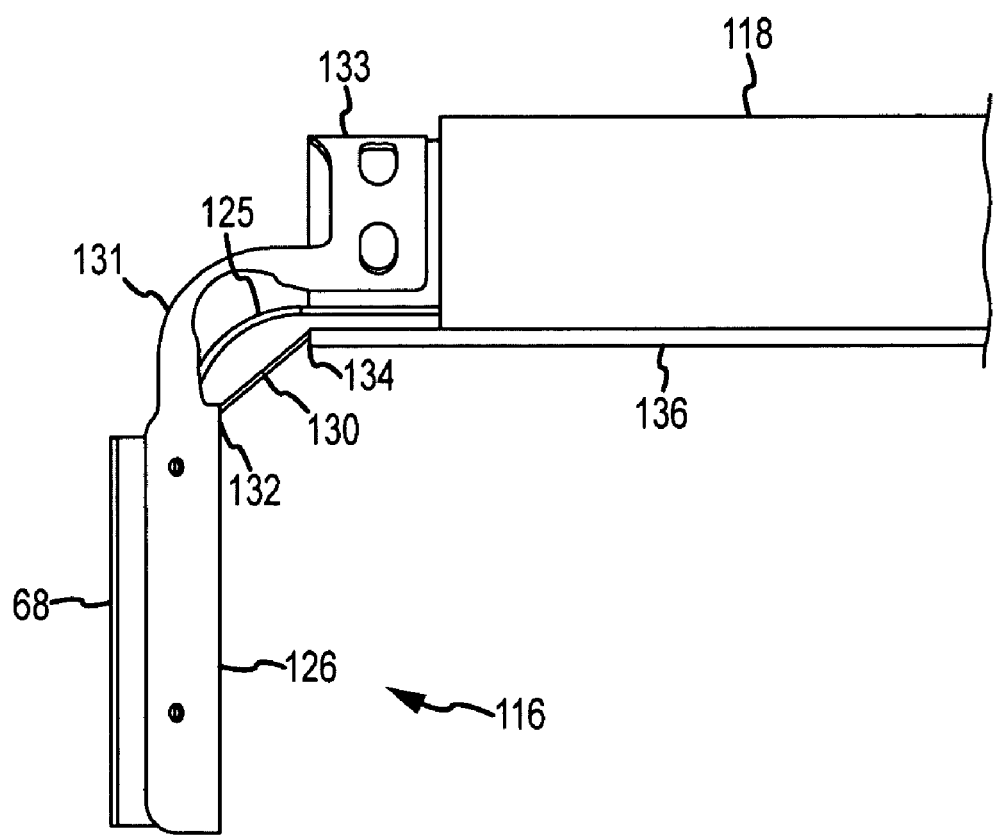

Deflection of the deflectable member 116 will now be discussed with reference to FIGS. 6B and 6C. FIGS. 6B and 6C illustrate the deflectable member 116 with the portion of the tip 120 surrounding the ultrasound image array 68 and support 126 removed. Also, the distal portion 124 of the outer tubular body 118 wrapped around the securement portion 133 has been removed. The support 126 may be configured similarly to the support 74 discussed above. The support 126 may further include a hinge portion 131 similar to the hinge portion 86.

To deflect the deflectable member 116 relative to the outer tubular body 118, the pull wire 130 may be moved relative to the outer tubular body 118. As shown in FIG. 6C, pulling the pull wire 130 (e.g., toward the handle 56) may impart a force on the support 126 at a pull wire anchor point 132 directed along the pull wire 130 toward a pull wire outlet 134. The pull wire outlet 134 is the point where the pull wire 130 emerges from a pull wire housing 136. The pull wire housing 136 may be fixed to the outer tubular body 118. Such a force may result in the deflectable member 116 bending toward the pull wire outlet 134. As in the embodiment illustrated in FIGS. 5C and 5D, the deflection of the deflectable member will be constrained by the hinge portion 131 of the support 126. As illustrated in FIG. 6C, the resultant deflection of the deflectable member 116 may result in the ultrasound transducer array 68 being pivoted to a forward-looking position. It will be appreciated that varying amounts of deflection of the deflectable member 116 may be achieved through controlled movement of the pull wire 130. In this regard, any deflection angle between 0 degrees and 90 degrees may be achievable by displacing the pull wire 130 a lesser amount than as illustrated in FIG. 6C. Furthermore, deflections of greater than 90 degrees may be obtainable by displacing the pull wire 130 a greater amount than as illustrated in FIG. 6C. As illustrated in FIGS. 6B and 6C, the flexboard 122 may remain interconnected to the outer tubular body 118 and the deflectable member 116 independent of the deflection of the deflectable member 116.

Figure 6D:
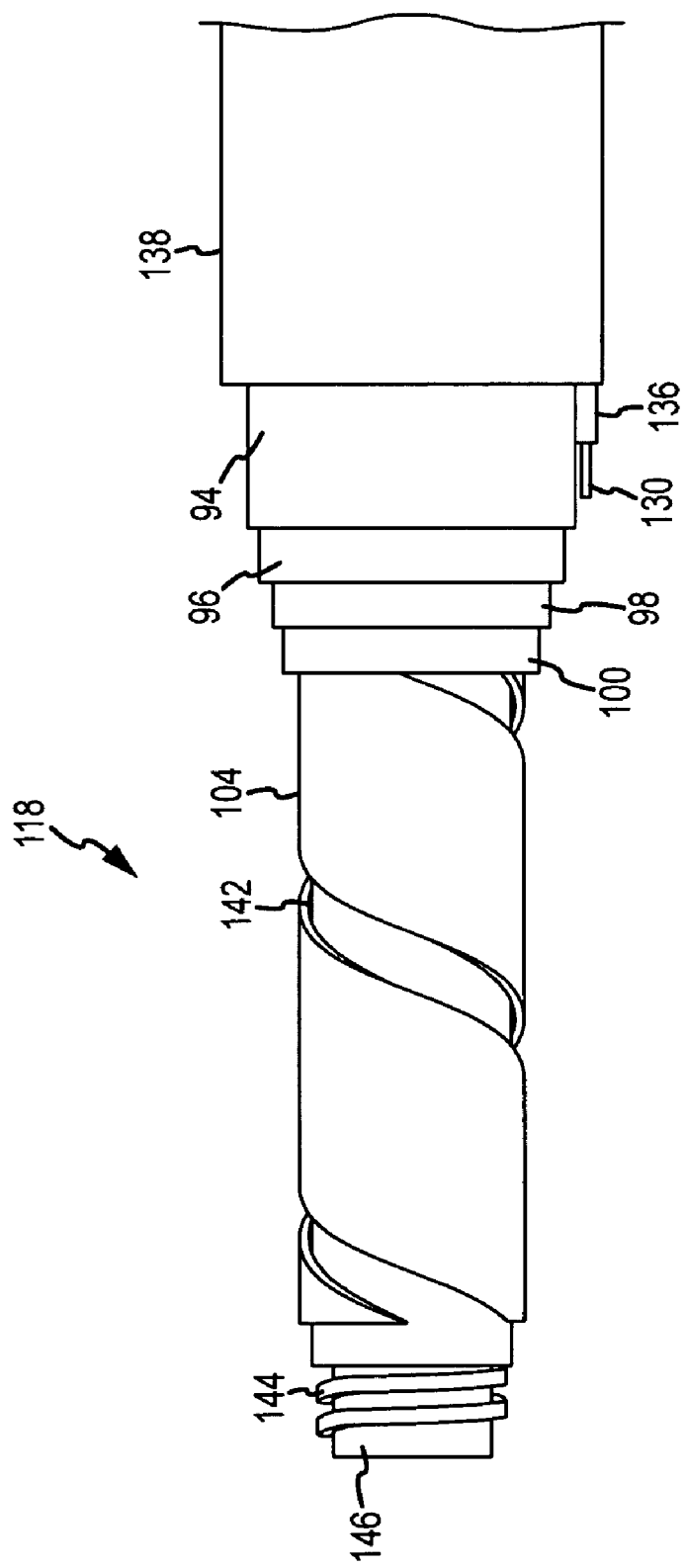

FIG. 6D illustrates an embodiment of the outer tubular body 118. For the illustration of FIG. 6D, portions of various layers have been removed to reveal the construction of the outer tubular body 118. Layers similar to those of the embodiment of FIG. 5E are labeled with the same reference numbers as in FIG. 5E and will not be discussed at length here. The pull wire housing 136 housing the pull wire 130 may be disposed proximate to the outer covering 94. An external wrap 138 may then be disposed over the outer covering 94 and pull wire housing 136 to secure the pull wire housing 136 to the outer covering 94. Alternatively, the pull wire housing 136 and pull wire 130 may, for example, be disposed between the outer covering 94 and the outer low-dielectric constant layer 96. In such an embodiment, the outer wrap 138 may not be needed. Other appropriate locations for the pull wire housing 136 and pull wire 130 may be utilized.

Disposed interior to the outer low-dielectric constant layer 96 may be the shield layer 98. A first tie layer (not shown in FIG. 6D), similar to first tie layer 97, may be disposed between the outer low-dielectric constant layer 96 and the shield layer 98. Disposed interior to the shield layer may be the second tie layer 100. Disposed interior to the second tie layer 100 may be the electrical interconnection member 104. Disposed interior to the electrical interconnection member 104 may be an inner low-dielectric constant layer 142. In this regard, the electrical interconnection member 104 may be helically disposed within the wall of the outer tubular body 118.

Moving toward the center of the outer tubular body 118, the next layer may be a coiled reinforcement layer 144. The coiled reinforcement layer 144 may, for example, comprise a stainless steel coil. In an exemplary embodiment, the coiled reinforcement layer 144 may be about 0.05-0.08 mm thick. Moving toward the center of the outer tubular body 118, the next layer may be an inner covering 146. The inner covering 146 may be configured similar to and serve a similar function as the outer covering 94. The lumen 128 may have a center axis aligned with the center axis of the outer tubular body 118.

As noted above, the wrapped layers of the distal portion 124 of the outer tubular body 118 may serve to secure the securement portion 133 of the support 126 to an inner portion of the outer tubular body 118. For example, each layer outboard of the electrical interconnection member 104 may be removed in the distal portion 124. Furthermore, the electrical interconnection member 104 may be electrically interconnected to the flexboard 122 proximal to the distal portion 124 in a manner similar to as described with reference to FIG. 5F. Accordingly, the securement portion 133 of the support 126 may be positioned over the remaining inner layers (e.g., the inner low-dielectric constant layer 142, the coiled reinforcement layer 144 and the inner covering 146) and a plurality of layers of material may be wrapped about the distal portion 124 to secure the securement portion 133 to the outer tubular body 118.

The outer diameter of the outer tubular body 118 may, for example, be about 12.25 Fr. The inner diameter of the outer tubular body 118 may, for example, be about 8.4 Fr.

Figure 7A:
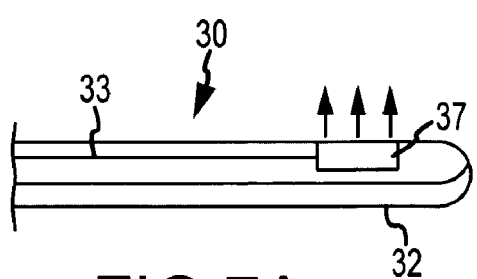
FIGS. 7A and 7B show a further aspect wherein an ultrasound transducer array is located near the distal end of the catheter. The array can be manipulated between side-looking and forward-looking by utilizing an actuation device attached to the array and extending to the proximal end of the catheter.
Figure 7B:
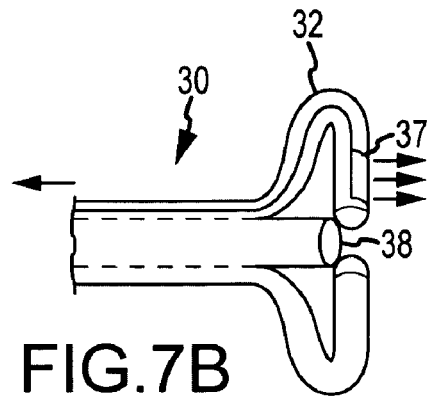

FIGS. 7A and 7B demonstrate further embodiments. As shown, the catheter 30 comprises a deflectable distal end 32. Located at deflectable distal end 32 is ultrasound transducer array 37. The catheter also includes wire 33 attached to the ultrasound transducer array 37 and extending to the proximal end of catheter 30 where it exits through a port or other opening at the proximal end of catheter 30. As shown in FIG. 7A, ultrasound transducer array 37 is in a "side-looking" configuration. The catheter can be delivered to the treatment site with the ultrasound transducer array 37 in the "side-looking" configuration, as shown in FIG. 7A. Once the treatment site is reached, wire 33 can be pulled in a proximal direction to deflect deflectable distal end 32 to result in ultrasound transducer array 37 being moved to a "forward-looking" configuration, as shown in FIG. 7B. As shown in FIG. 7B, once ultrasound transducer array 37 is positioned in the "forward-looking" position and deflectable distal end 32 is deflected as shown, generally centrally located lumen 38 is then available for delivery of a suitable interventional device to a point distal to the catheter distal end 32. Alternatively, a tube containing lumen 38 and movable relative to the outer surface of the catheter 30 may be used to deflect the deflectable distal end 32 to the "forward-looking" configuration.

Figure 8A:
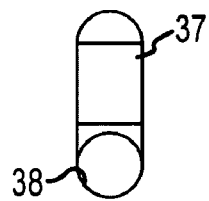
FIGS. 8A through 8D show various exemplary variations of the catheter of FIGS. 7A and 7B.
Figure 8B:
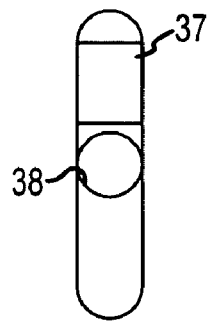
Figure 8C:
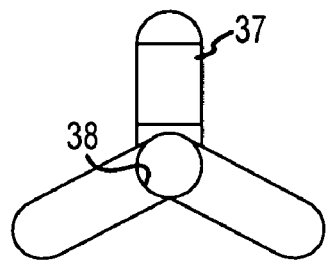
Figure 8D:
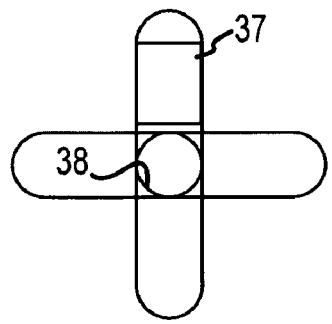

FIG. 8A is a front view of a single lobe configuration of the device shown in FIGS. 7A and 7B. FIG. 8B shows a dual-lobe configuration of the catheter shown in FIGS. 7A and 7B. FIG. 8C shows a tri-lobe configuration and FIG. 8D shows a quad-lobe configuration. As will be understood, any suitable number of lobes can be constructed as desired. Moreover, in multiple-lobe configurations, ultrasound transducer arrays 37 may be disposed on one or more of the lobes.

Figure 9:
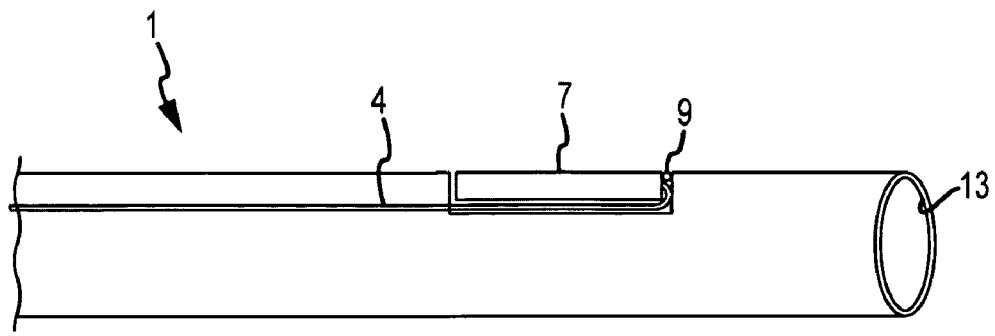
FIGS. 9, 9A and 9B demonstrate further embodiments wherein an ultrasound array is deflectable.
Figure 9A:
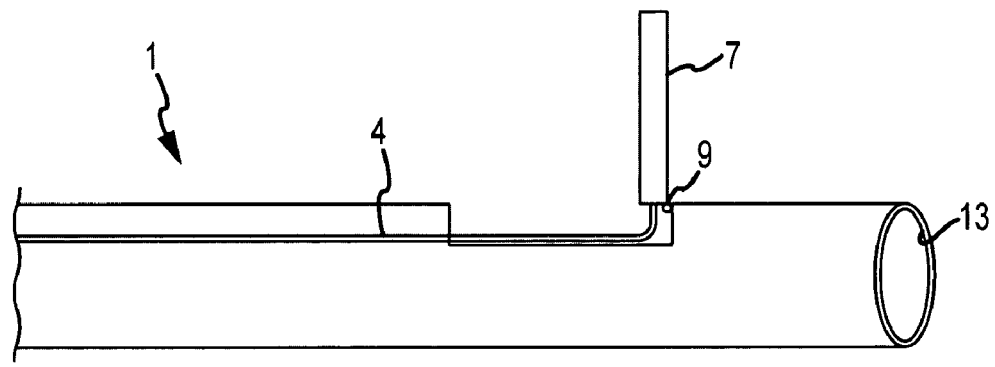
Figure 9B:
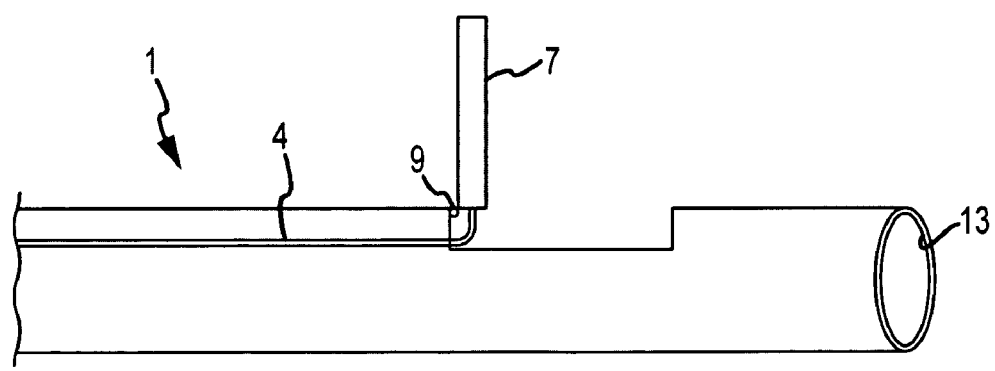

Further embodiments are shown in FIGS. 9, 9A and 9B. FIG. 9 shows catheter 1 having an ultrasound transducer array 7 near the distal end thereof. The ultrasound transducer array 7 is attached to catheter 1 by hinge 9. Electrically conductive wires 4 are connected to ultrasound transducer array 7 and extend proximally to the proximal end of the catheter 1. The catheter 1 includes distal exit port 13. The hinge 9 can be located at the distal end of ultrasound transducer array 7, as shown in FIG. 9A, or at the proximal end of ultrasound transducer array 7, as shown in FIG. 9B. In any event, the ultrasound transducer array 7 can be either passively or actively deflectable, as discussed above. Ultrasound transducer array 7 can be deflected up to the forward-looking configuration (as shown in FIGS. 9A and 9B) and an interventional device can be advanced at least partially out of distal exit port 13, such that at least a portion of the interventional device will be in the field of view of the ultrasound transducer array 7.

FIGS. 10A and 10B demonstrate a further embodiment where the catheter includes ultrasound transducer array 7 near the catheter distal end 2 of the catheter. The catheter further includes steerable segment 8 and lumen 10. Lumen 10 can be sized to accept a suitable interventional device that can be inserted at the proximal end of the catheter and advanced through lumen 10 and out port 13. The catheter can further include guidewire receiving lumen 16. Guidewire receiving lumen 16 can include proximal port 15 and distal port 14, thus allowing for the well known "rapid exchange" of suitable guidewires.

As further demonstrated in FIGS. 11 and 11A and 11B, the catheter steerable segment 8 can be bent in any suitable direction. For example, as shown in FIG. 11A the steerable segment is bent away from port 13 and as shown in FIG. 11B the steerable segment is bent toward port 13.

Figure 12:
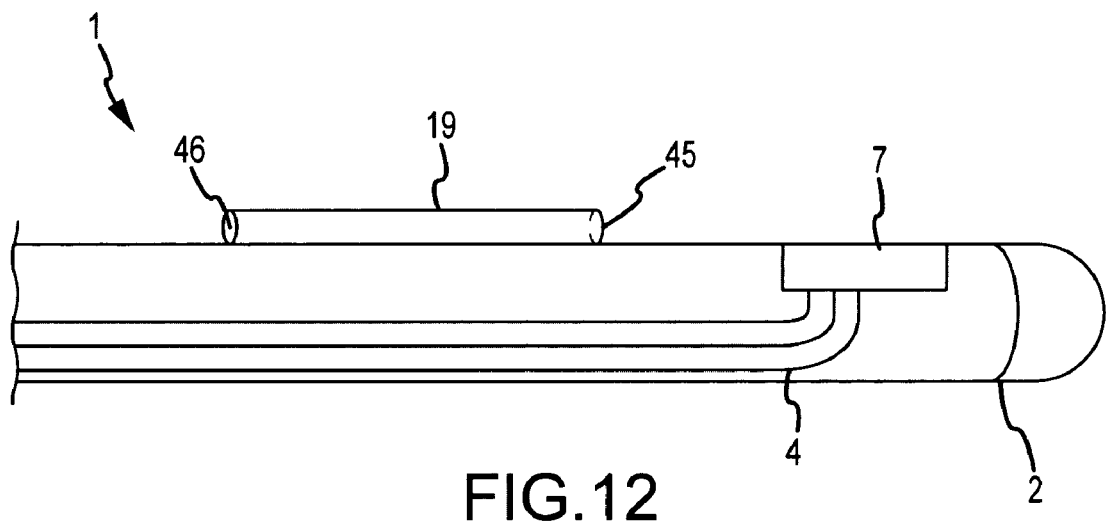
FIG. 12 demonstrates a still further embodiment.

FIG. 12 demonstrates yet another embodiment. Specifically, catheter 1 can include ultrasound transducer array 7 located at the distal end 2 of the catheter 1. Electrically conductive wires 4 are attached to the ultrasound transducer array 7 and extend to the proximal end of the catheter 1. Lumen 19 is located proximal to the ultrasound transducer array 7 and includes proximal port 46 and distal port 45. The lumen 19 can be sized to accept a suitable guidewire and/or interventional device. Lumen 19 can be constructed of a suitable polymer tube material, such as ePTFE. The electrically conductive wires 4 can be located at or near the center of the catheter 1.

Figure 13:
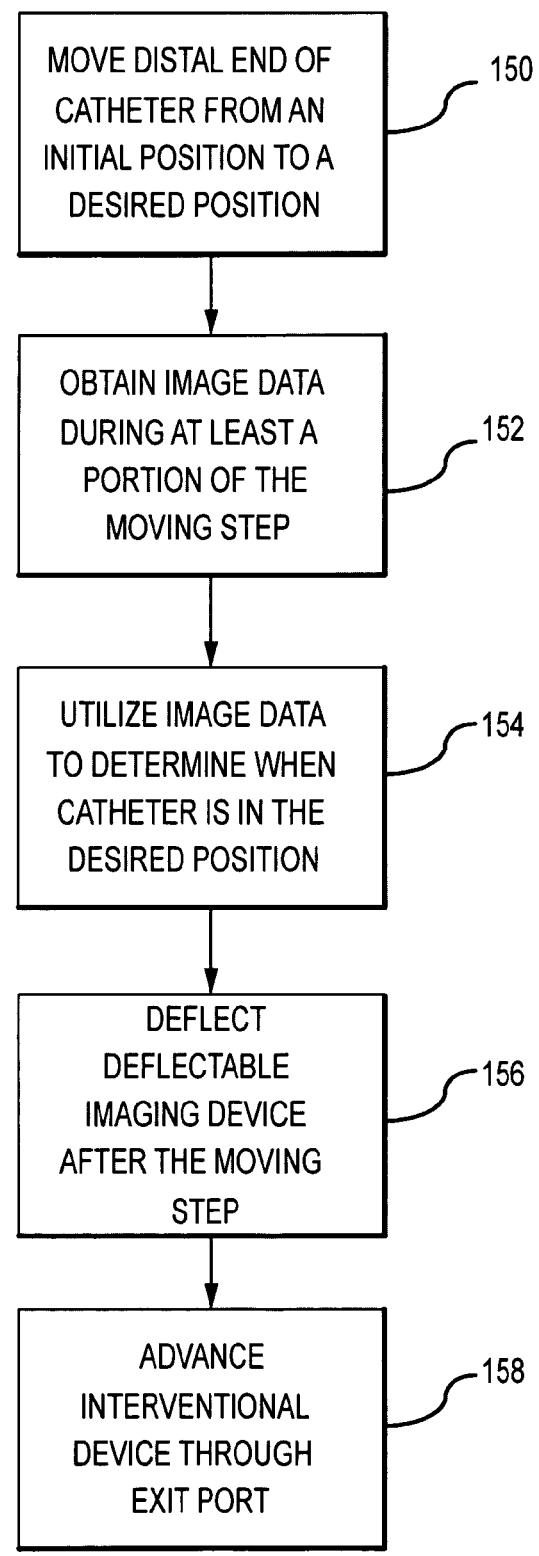
FIG. 13 is a flow chart for an embodiment of a method of operating a catheter.

FIG. 13 is a flow chart for an embodiment of a method of operating a catheter having a deflectable imaging device located at a distal end thereof. The first step 150 in the method may be to move the distal end of the catheter from an initial position to a desired position, wherein the deflectable imaging device is located in a first position during the moving step. The deflectable imaging device may be side-looking when in the first position. The moving step may include introducing the catheter into a body through an entry site that is smaller than the aperture of the deflectable imaging device. The moving step may include rotating the catheter relative to its surroundings.

The next step 152 may be to obtain image data from the deflectable imaging device during at least a portion of the moving step. The obtaining step may be performed with the deflectable imaging device located in the first position. During the moving and obtaining steps, a position of the deflectable imaging device relative to the distal end of the catheter may be maintained. Thus the deflectable imaging device may be moved and images may be obtained without moving the deflectable imaging device relative to the distal end of the catheter. During the moving step, the catheter, and therefore the deflectable imaging device, may be rotated relative to its surroundings. Such rotation may allow the deflectable imaging device to obtain images in a plurality of different directions transverse to the path traveled by the catheter during the moving step.

The next step 154 may be to utilize the image data to determine when the catheter is located at the desired position. For example, the image data may indicate the position of the deflectable imaging device, and therefore the distal end of the catheter, relative to a landmark (e.g., an anatomical landmark).

The next step 156 may be to deflect the deflectable imaging device from the first position to a second position. The deflecting step may follow the moving step. The deflectable imaging device may be forward-looking in the second position. The deflectable imaging device may be angled at least 45 degrees relative to a center axis of the catheter when in the second position. Optionally, after the deflecting step, the deflectable imaging device may be returned to the first position and the catheter repositioned (e.g., repeating the moving step 150, the obtaining step 152, and the utilizing step 154). Once repositioned, the deflecting step 156 may be repeated and the method may be continued.

In an embodiment, the catheter may comprise an outer tubular body and an activation device, each extending from a proximal end to the distal end of the catheter. In such an embodiment, the deflecting step may include translating a proximal end of at least one of the outer tubular body and actuation device relative to a proximal end of the other one of the outer tubular body and actuation device. The deflectable imaging device may be supportably interconnected by a hinge to one of the outer tubular body and the actuation device, and the deflecting step may further comprise applying a deflection force to the hinge in response to the translating step. Furthermore, the deflecting step may further include initiating the application of the deflection force to the hinge in response to the translating step. The deflection force may be applied and then maintained by manipulating a handle interconnected to the proximal end of the catheter. Moreover, the applying step may comprise communicating the deflection force by the actuation device from the proximal end to the distal end of the catheter in a balanced and distributed manner about a center axis of the outer tubular body.

The next step 158 may be to advance an interventional device through an exit port at the distal end of the catheter and into an imaging field of view of the deflectable imaging device in the second position. The imaging field of view may be maintained in substantially fixed registration to the distal end of the catheter during the advancing step.

After advancing and using the interventional device (e.g., to perform a procedure, to install or retrieve a device, to make a measurement), the interventional device may be withdrawn through the exit port. The deflectable imaging device may then be returned to the first position. The return to the first position may be facilitated by an elastic deformation quality of the hinge. For example, the hinge may be biased toward positioning the deflectable imaging device in the first position. As such, when the deflectable imaging device is in the second position and the deflection force is removed, the deflectable imaging device may return to the first position. After withdrawal of the interventional device through the exit port (and optionally from the entire catheter) and return of the deflectable imaging device to the first position, the catheter may then be repositioned and/or removed.

Additional modifications and extensions to the embodiments described above will be apparent to those skilled in the art. Such modifications and extensions are intended to be within the scope of the present invention as defined by the claims that follow.

What is claimed is:

1. A catheter comprising:
   an outer tubular body having a proximal end and a distal end;
   an inner tubular body having a proximal end and a distal end, the inner tubular body positioned within the outer tubular body and extending from the proximal end of the outer tubular body to the distal end of the outer tubular body, the inner tubular body defining a lumen therethrough for delivering an interventional device extending from the proximal end of the inner tubular body to an exit port located at the distal end of the inner tubular body, wherein the outer tubular body and inner tubular body are disposed for selective relative movement therebetween;
   a deflectable imaging device, at least a portion of which is permanently located distal to the distal end of the outer tubular body;
   a hinge supportably interconnected to the distal end of one of the inner tubular body and the outer tubular body and restrainably interconnected to the distal end of the other one of the inner tubular body and the outer tubular body, wherein the deflectable imaging device is supportably interconnected to the hinge; and
   wherein upon the selective relative movement, the deflectable imaging device is selectively deflectable in a predetermined manner.

2. The catheter of claim 1, wherein engagement between surfaces of the inner tubular body and the outer tubular body provides a mechanism interface sufficient to maintain a selected relative position between the inner tubular body and the outer tubular body and corresponding deflected position of the deflectable imaging device.

3. The catheter of claim 1, wherein the hinge is supportably interconnected to the inner tubular body and restrainably interconnected to the outer tubular body.

4. The catheter of claim 3, wherein said deflectable imaging device is selectively deflectable away from a center axis of said outer tubular body upon said selective relative movement of the outer tubular body and inner tubular body.

5. The catheter of claim 3, wherein said deflectable imaging device is selectively deflectable away from a center axis of said outer tubular body, at least partially distal to a distal end of said out tubular body, upon said selective relative movement of the outer tubular body and inner tubular body.

6. The catheter of claim 3, wherein the deflectable imaging device is deflectable about a deflection axis that is offset from a center axis of the outer tubular body.

7. The catheter of claim 6, wherein the deflection axis lies in a plane orthogonal to the center axis.

8. The catheter of claim 1, wherein the hinge is restrainably interconnected to the distal end of the outer tubular body, wherein upon advancement of the inner tubular body relative to the outer tubular body, a deflection force is communicated to the deflectable imaging device by the restraining member.

9. The catheter of claim 1, wherein any movement of the inner tubular body relative to the outer tubular body produces a corresponding deflection of the deflectable imaging device.

10. The catheter of claim 9, wherein a relationship between the movement of the inner tubular body relative to the outer tubular body and the corresponding deflection of the deflectable imaging device is linear.

11. The catheter of claim 1, wherein the selective relative movement is resultant from an actuation force, wherein the actuation force is balanced and distributed about a center axis of the outer tubular body.

12. The catheter of claim 1, wherein a center axis of the outer tubular body coincides with a center axis of the inner tubular body.

13. The catheter of claim 1, wherein said deflectable imaging device is selectively deflectable away from a center axis of said outer tubular body upon said selective relative movement of the outer tubular body and inner tubular body.

14. The catheter of claim 1, wherein said deflectable imaging device is selectively deflectable away from a center axis of said outer tubular body, at least partially distal to a distal end of said out tubular body, upon said selective relative movement of the outer tubular body and inner tubular body.

15. The catheter of claim 1, wherein said deflectable imaging device is selectively deflectable away from a center axis of said outer tubular body, entirely distal to a distal end of said outer tubular body, upon said selective relative movement of the outer tubular body and inner tubular body.

16. The catheter of claim 1, wherein the deflectable imaging device is deflectable about a deflection axis that is offset from a center axis of the outer tubular body.

17. The catheter of claim 16, wherein the deflection axis lies in a plane transverse to the center axis.

18. The catheter of claim 17, wherein the deflection axis lies in a plane orthogonal to the center axis.

19. The catheter of claim 1, wherein the exit port has a center axis coaxially aligned with a center axis of the outer tubular body.

20. The catheter of claim 19, wherein said deflectable imaging device is selectively deflectable away from the coaxial center axes.

* * * * *